US007262302B2

(12) United States Patent
Mercep et al.

(10) Patent No.: US 7,262,302 B2
(45) Date of Patent: Aug. 28, 2007

(54) 1-THIA-3-AZA-DIBENZOAZULENES AS INHIBITORS OF TUMOUR NECROSIS FACTOR PRODUCTION AND INTERMEDIATES FOR THE PREPARATION THEREOF

(75) Inventors: Mladen Mercep, Zagreb (HR); Milan Mesic, Zagreb (HR); Marina Modric, Zagreb (HR); Dijana Pesic, Sibenik (HR); Davor Kidemet, Varazdin (HR)

(73) Assignee: GlaxoSmithKline Istrazivacki Centar Zagreb, D.O.O. (HR)

( * ) Notice: Subject to any disclaimer, the term of this patent is extended or adjusted under 35 U.S.C. 154(b) by 0 days.

(21) Appl. No.: 10/515,700

(22) PCT Filed: May 20, 2003

(86) PCT No.: PCT/HR03/00023

§ 371 (c)(1),
(2), (4) Date: Jul. 26, 2005

(87) PCT Pub. No.: WO03/099827

PCT Pub. Date: Dec. 4, 2003

(65) Prior Publication Data

US 2006/0111340 A1 May 25, 2006

(30) Foreign Application Priority Data

May 23, 2002 (HR) .......................... P 20020451 A

(51) Int. Cl.
*C07D 277/60* (2006.01)
*C07D 513/02* (2006.01)
*C07D 487/02* (2006.01)

(52) U.S. Cl. ...................................... 548/149; 540/578

(58) Field of Classification Search ................. 548/149
See application file for complete search history.

(56) References Cited

U.S. PATENT DOCUMENTS

| | | |
|---|---|---|
| 3,711,489 A | 1/1973 | Lombardino |
| 4,198,421 A | 4/1980 | Cherkofsky et al. |

FOREIGN PATENT DOCUMENTS

| | | |
|---|---|---|
| CA | 967573 | 5/1975 |
| HR | 20000310 | 2/2002 |
| WO | WO-01/87890 | 11/2001 |

OTHER PUBLICATIONS

Cecil Textbook of Medicine, 20th edition (1996), vol. 2, pp. 2050-2057.*

Cecil Textbook of Medicine, 20th edition (1996), vol. 2, pp. 1992-1996.*

FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*

Mrak, et al. Potential Inflammatory biomarkers in Alzheimer's disease. Journal of Alzheimer's Disease, 2005, 8, 369-375.*

Kovtunenko, et al. Synthesis of thiazoles according to Hantzsch from 11-bromo-10, 11-dihydrodibenz[b,f] thienpin-10-ones. Ukrainskii Khimicheskii Zhurnal. 1983, 49, 975-978.*

Cagniant and Kirsch, C.R. Acad. Sc. Paris, 1976, 283:683-686.

Kovtunenko et al., Ukr. Khim. Zh., 1983, 43:975-978.

Bresnihan, Treatment with Recombinant Human Interleukin-1 Receptor Antagonist (rhlL-1ra) in Rheumatoid Arthritis (RA); Results of a Randomized Double-Blind, Placebo-Controlled Multicenter trial, Arthrit. Rheum., 1996, 39:73.

Mori et al., Attenuation of Collagen-Induced Arthritis in 55-kDa TNF Receptor Type 1 (TNFR1)-IgG1-Treated and TNFR1-Deficient Mice, J. Immunol., 1996, 157:3178-3182.

Van Assche and Rutgeerts, Anti-TNF agents in Crohn's disease, Exp. Opin. Invest. Drugs, 2000, 9:103-111.

Keffer at al., Transgenic mice expressing human tumour necrosis factor: a predictive genetic model of arthritis, EMBO J., 1991, 10:4025-4031.

Elliott et al., Randmoised double-blind comparsion of chimeric monoclonal antibody to tumor necrosis factor alpha (cA2) versus placebo in rheumatoid arthritis, The Lancet, 1994, 344:1105-1110.

Carswell et al., An endotoxin-induced serum factor that causes necrosis of tumors, Proc. Natl. Acad. Sci. U.S.A., 1975, 72:3666-3670.

Dinarello, An Update on Human Interleukin-1: From Molecular Biology to Clinical Relevance, J. Clinical Immunology, 1985, 5:287.

Georgopoulos et al., Transmembrane TNF Is Sufficient To Induce Localized Tissue Toxicity and Chronic Inflammatory Arthritis In Transgenic Mice, J. Inflamm., 1996, 46:86-97.

Dinarello, Interleukin-1, Rev. Infect Disease, 1984, 6(1):51-95.

Pfeffer et al., Mice Deficient for the 55kd Tumor Necrosis Factor Receptor Are Resistant to Endotixic Shock, yet Succumb to L. monocytogenes Infection, Cell, 1993, 73:457-467.

Teitei, The Synthesis of 2-(5-Phenylthiazol-4-yl)benzoic Acids, Aust. J. Chem., 1980, 33:605-611.

(Continued)

*Primary Examiner*—Rebecca Anderson
*Assistant Examiner*—Shawquia Young
(74) *Attorney, Agent, or Firm*—J. Scott Young

(57) ABSTRACT

The present invention relates to derivatives of 1-thia-3-aza-dibenzoazulene class, to their pharmacologically acceptable salts and solvates, to processes and intermediates for the preparation thereof as well as to their antiinflammatory effects, especially to the inhibition of tumour necrosis factor-α (TNF-α) production and the inhibition of interleukin-1 (IL-1) production as well as to their analgetic action.

14 Claims, No Drawings

OTHER PUBLICATIONS

Mattioli and Ghia, omega-Dialkylaminoalkyl Ethers of Phenyl-(5-substituted 1-phenyl-1H-pyrazol-4-yl) methanols with Analgesic and Anti-inflammatory Activity, J. Heterocyclic Chem., 1997, 34:963-968.

Collier et al., The Abdominal Constriction Response and Its Suppression By Analgesic Drugs in the Mouse, Br. J. Pharmac. Chemother., 1968, 32:295-310.

Schweizer et al., Combined automated writhing/motility test for testing analgesics, Agents and Actions, 1988, 23:29-31.

Fukawa et al., A Method for Evaluating Analgesic Agents in Rats, J. Pharmacol. Meth., 1980, 4:251-259.

Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, J. Pharmac. Env. Therap., 1996, 279(3):1453-1461.

* cited by examiner

1-THIA-3-AZA-DIBENZOAZULENES AS INHIBITORS OF TUMOUR NECROSIS FACTOR PRODUCTION AND INTERMEDIATES FOR THE PREPARATION THEREOF

This application is a National Stage under 35 U.S.C. §371 of PCT International Application No. PCT/HR03/00023, filed May 20, 2003, which claims the benefit under 35 U.S.C. §119(e) of prior Croatian Application No. P20020451A, filed May 23, 2002, the entire contents of which are incorporated herein by reference.

TECHNICAL FIELD

The present invention relates to 1-thia-3-aza-dibenzoazulene derivatives, to their pharmacologically acceptable salts and solvates, to processes and intermediates for the preparation thereof as well as to their antiinflammatory effects, especially to the inhibition of tumour necrosis factor-α (TNF-α) production and the inhibition of interleukin-1 (IL-1) production as well as to their analgetic action.

PRIOR ART

Some 1,3-diaza-dibenzoazulene derivatives and salts thereof are known as a novel class of compounds having an antiinflammatory action (U.S. Pat. Nos. 3,711,489, 4,198,421 and CA 967,573). From the class of 1-thia-dibenzoazulenes, in the literature there are described derivatives substituted in 2-position with methyl, methyl-ketone, nitro group or with carboxylic group derivatives (Cagniant P G, *C. R. Hebd. Sceances Acad. Sci.,* 1976, 283:683-686) and 1-thia-dibenzoazulene derivatives having alkyloxy substituents in 2-position (WO 01/878990), which also possess strong antiinflammatory action.

According to our knowledge and to available literature data, derivatives of 1,8-dithia-3-aza-dibenzoazulenes having in 2-position an amino group are well-known (Kovtunenko V A et al., *Ukr. Khim. Zh.,* 1983 43:975-978), whereas other derivatives and especially those having alkyl or some other groups, which are alkyl derivatives and intermediates for the preparation thereof, in 2-position have now been prepared and described for the first time. It has not been known either that dibenzoazulenes from the class of thiazoles show antiinflammatory action (inhibitors of TNF-α production, inhibitors of IL-1 production) and/or analgetic action.

TNF-α is defined as a serum factor induced by endotoxin and causing tumour necrosis in vitro and in vivo (Carswell E A et al., *Proc. Natl. Acad. Sci. U.S.A.,* 1975, 72:3666-3670). Besides an antitumour action, TNF-α also possesses numerous other biological actions important in the homeostasis of an organism and in pathophysiological conditions. The main sources of TNF-α are monocytes-macrophages, T-lymphocytes and mastocytes.

The discovery that anti-TNF-α antibodies (cA2) have an action in treating patients with rheumatoid arthritis (RA) (Elliott M et al., *Lancet,* 1994, 344:1105-1110) led to an increased interest in finding novel TNF-α production inhibitors as possible potent drugs for RA. Rheumatoid arthritis is an autoimmune chronic inflammatory disease characterized by irreversible pathological changes in the joints. Besides in RA, TNF-α antagonists may also be used in numerous pathological conditions and diseases such as spondylitis, osteoarthritis, gout and other arthritic conditions, sepsis, septic shock, toxic shock syndrom, atopic dermatitis, contact dermatitis, psoriasis, glomerulonephritis, lupus erythematosus, scleroderma, asthma, cachexia, chronic obstructive lung disease, congestive cardiac arrest, insulin resistance, lung fibrosis, multiple sclerosis, Crohn's disease, ulcerative colitis, viral infections and AIDS.

Some of the proofs indicating the biological importance of TNF-α were obtained by in vivo experiments in mice, in which mice gens for TNF-α or its receptor were inactivated. Such animals are resistant to collagen-induced arthritis (Mori L et al., *J. Immunol.,* 1996, 157:3178-3182) and to endotoxin-caused shock (Pfeffer K et al., *Cell,* 1993, 73:457-467). In animal experiments where TNF-α level was increased, a chronic inflammatory polyarthritis similar to RA occurred (Georgopoulos S et al., *J. Inflamm.,* 1996, 46:86-97; Keffer J et al., *EMBO J.,* 1991, 10:4025-4031) and its clinical picture was alleviated by inhibitors of TNF-α production. The treatment of such inflammatory and pathological conditions usually includes the application of non-steroid antiinflammatory drugs and, in more severe cases, gold salts, D-penicillinamine or methotrexate are administered. Said drugs act symptomatically, but they do not stop the pathological process. Novel approaches in the therapy of rheumatoid arthritis are based upon drugs such as tenidap, leflunomide, cyclosporin, FK-506 and upon biomolecules neutralizing the TNF-α action. At present there are commercially available etanercept (Enbrel, Immunex/Wyeth), a fusion protein of the soluble TNF-α receptor, and infliximab (Remicade, Centocor), a chimeric monoclonal human and mouse antibody. Besides in RA therapy, etanercept and infliximab are also registered for the therapy of Crohn's disease (*Exp. Opin. Invest. Drugs,* 2000, 9:103).

In an optimal RA therapy, besides inhibition of TNF-α secretion, also the inhibition of IL-1 production is very important since IL-1 is an important cytokin in cell regulation and immunoregulation as well as in pathophysiological conditions such as inflammation (Dinarello C A et al., *Rev. Infect. Disease,* 1984, 6:51). Well-known biological activities of IL-1 are: activation of T-cells, induction of elevated temperature, stimulation of secretion of prostaglandine or collagenase, chemotaxia of neutrophils and reduction of iron level in plasma (Dinarello C A, *J. Clinical Immunology,* 1985, 5:287). Two receptors to which IL-1 may bind are well-known: IL-1RI and IL-1RII. IL-1RI transfers a signal intracellularly, whereas IL-1RII, though situated on the cell surface, does not transfer a signal inside the cell. Since IL1-RII binds IL-1 as well as IL1-RI, it may act as a negative regulator of IL-1 action. Besides this mechanism of signal transfer regulation, another natural antagonist of IL-1 receptor (IL-1ra) is present in cells. This protein binds to IL-1RI but does not bring about a stimulation thereof. The potency of IL-1ra in stopping the signal transfer stimulated by IL-1 is not high and its concentration has to be 500 times higher than that of IL-1 in order to achieve a break in the signal transfer. Recombinant human IL-1ra (Amgen) was clinically tested (Bresnihan B et al., *Arthrit. Rheum.,* 1996, 39:73) and the obtained results indicated an improvement of the clinical picture in RA patients over a placebo. These results indicate the importance of the inhibition of IL-1 action in treating diseases such as RA where IL-1 production is disturbed. Since there exists a synergistic action of TNF-α and IL-1, dual TNF-α and IL-1 inhibitors may be used in treating conditions and diseases related to an enhanced production of TNF-α and IL-1.

Solution of Technical Problem

The present invention relates to 1-thia-3-aza-dibenzoazulenes of the formula I

I

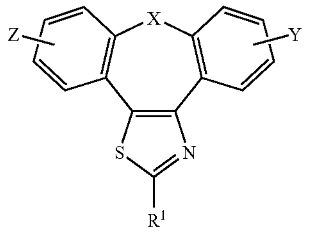

wherein

X may be $CH_2$ or a hetero atom such as O, S, S(=O), $S(=O)_2$, or $NR^a$, wherein $R^a$ is hydrogen or a protecting group;

Y and Z independently from each other denote one or more identical or different substituents linked to any available carbon atom and may be hydrogen, halogen, $C_1$-$C_4$ alkyl, $C_2$-$C_4$ alkenyl, $C_2$-$C_4$ alkinyl, halo-$C_1$-$C_4$ ailcyl, hydroxy, $C_1$-$C_4$ alkoxy, trifluoromethoxy, $C_1$-$C_4$ alkanotyl, amino, amino-$C_1$-$C_4$ alkyl, $C_1$-$C_4$ alkylamino, N-($C_1$-$C_4$-alkyl) amino, N,N-di ($C_1$-$C_4$-alkyl)amino, thiol, $C_1$-$C_4$ alkylthio, sulfonyl, $C_1$-$C_4$ alkylsulfonyl, sulfinyl, $C_1$-$C_4$ alkylsulfinyl, carboxy, $C_1$-$C_4$alkoxycarbonyl, cyano, nitro;

$R^1$ may be hydrogen, halogen, an optionally substituted $C_1$-$C_7$ alkyl or $C_2$-$C_7$ alkenyl, $C_2$-$C_7$ alkinyl, an optionally substituted aryl or heteroaryl and a heterocycle, hydroxy, hydroxy-$C_2$-$C_7$ alkenyl, hydroxy-$C_2$-$C_7$ alkinyl, $C_1$-$C_7$ alkoxy, thiol, thio-$C_2$-$C_7$ alkenyl, thio-$C_2$-$C_7$ alkinyl, $C_1$-$C_7$ alkylthio, amino-$C_2$-$C_7$ alkenyl, amino-$C_2$-$C_7$ alkinyl, amino-$C_1$-$C_7$ alkoxy, $C_1$-$C_7$ alkanoyl, aroyl, oxo-$C_1$-$C_7$ alkyl, $C_1$-$C_7$ alkanoyloxy, carboxy, an optionally substituted ($C_1$-$C_7$ alkyloxycarbonyl or aryloxycarbonyl), carbamoyl, N-($C_1$-$C_7$-alkyl)carbamoyl, N,N-di($C_1$-$C_7$-alkyl)carbamoyl, cyano, cyano-$C_1$-$C_7$ alkyl, sulfonyl, $C_1$-$C_7$ alkylsulfonyl, sulfinyl, $C_1$-$C_7$ alkylsulfinyl, nitro, or a substituent of the formula II

II

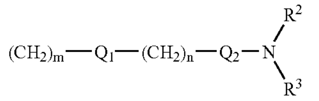

wherein $R^2$ and $R^3$ simultaneously or independently from each other may be hydrogen, $C_1$-$C_4$ alkyl, aryl or together with N have the meaning of an optionally substituted heterocycle or heteroaryl;

m represents an integer from 1 to 3;

n represents an integer from 0 to 3;

$Q_1$ and $Q_2$ represent, independently from each other, oxygen, sulfur or groups:

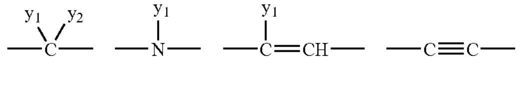

wherein the substituents $y_1$ and $y_2$ independently from each other may be hydrogen, halogen, an optionally substituted $C_1$-$C_4$ alkyl or aryl, hydroxy, $C_1$-$C_4$ alkoxy, $C_1$-$C_4$ alkanoyl, thiol, $C_1$-$C_4$ alkylthio, sulfonyl, $C_1$-$C_4$ alkylsulfonyl, sulfinyl, $C_1$-$C_4$ alkylsulfinyl, cyano, nitro or together form a carbonyl or imino group;

as well as to pharmacologically acceptable salts and solvates thereof.

The term "halo", "hal" or "halogen" relates to a halogen atom which may be fluorine, chlorine, bromine or iodine.

The term "alkyl" relates to alkyl groups with the meaning of alkanes wherefrom radicals are derived, which radicals may be straight, branched or cyclic or a combination of straight and cyclic ones and branched and cyclic ones. The preferred straight or branched alkyls are e.g. methyl, ethyl, propyl, isopropyl, butyl, sec-butyl and tert-butyl. The preferred cyclic alkyls are e.g. cyclopentyl or cyclohexyl.

The term "haloalkyl" relates to alkyl groups which must be substituted with at least one halogen atom. The most frequent haloalkyls are e.g. chloromethyl, dichloromethyl, trifluoromethyl or 1,2-dichloropropyl.

The term "alkenyl" relates to alkenyl groups having the meaning of hydrocarbon radicals, which may be straight, branched or cyclic or are a combination of straight and cyclic ones or branched and cyclic ones, but having at least one carbon-carbon double bond. The most frequent alkenyls are ethenyl, propenyl, butenyl or cyclohexenyl.

The term "alkinyl" relates to alkinyl groups having the meaning of hydrocarbon radicals, which are straight or branched and contain at least one and at most two carbon-carbon triple bonds. The most frequent alkinyls are e.g. ethinyl, propinyl or butinyl.

The term "alkoxy" relates to straight or branched chains of alkoxy group. Examples of such groups are methoxy, propoxy, prop-2-oxy, butoxy, but-2-oxy or methylprop-2-oxy.

The term "aryl" relates to groups having the meaning of an aromatic ring, e.g. phenyl, as well as to fused aromatic rings. Aryl contains one ring with at least 6 carbon atoms or two rings with totally 10 carbon atoms and with alternating double (resonant) bonds between carbon atoms. The most freqently used aryls are e.g. phenyl or naphthyl. In general, aryl groups may be linked to the rest of the molecule by any available carbon atom via a direct bond or via a $C_1$-$C_4$ alkylene group such as methylene or ethylene.

The term "heteroaryl" relates to groups having the meaning of aromatic and partially aromatic groups of a monocyclic or bicyclic ring with 4 to 12 atoms, at least one of them being a hetero atom such as O, S or N, and the available nitrogen atom or carbon atom is the binding site of the group to the rest of the molecule either via a direct bond or via a $C_1$-$C_4$ alkylene group defined earlier. Examples of this type are thiophenyl, pyrrolyl, imidazolyl, pyridinyl, oxazolyl, thiazolyl, pyrazolyl, tetrazolyl, pirimidinyl, pyrazinyl, quinolinyl or triazinyl.

The term "heterocycle" relates to five-member or six-member, fully saturated or partly unsaturated heterocyclic groups containing at least one hetero atom such as O, S or N, and the available nitrogen atom or carbon atom is the binding site of the group to the rest of the molecule either via a direct bond or via a $C_1$-$C_4$ alkylene group defined earlier. The most frequent examples are morpholinyl, piperidyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The term "optionally substituted alkyl" relates to alkyl groups which may be optionally additionally substituted with one, two, three or more substituents. Such substituents may be halogen atom (preferably fluorine or chlorine), hydroxy, $C_1$-$C_4$ alkoxy (preferably methoxy or ethoxy), thiol, $C_1$-$C_4$ alkylthio (preferably methylthio or ethylthio), amino, N-($C_1$-$C_4$) alkylamino (preferably N-methylamino or N-ethylamino), N,N-di($C_1$-$C_4$-alkyl)-amino (preferably dimethylamino or diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

The term "optionally substituted alkenyl" relates to alkenyl groups optionally additionally substituted with one, two or three halogen atoms. Such substituents may be e.g. 2-chloroethenyl, 1,2-dichloroethenyl or 2-bromo-propene-1-yl.

The term "optionally substituted aryl, heteroaryl or heterocycle" relates to aryl, heteroaryl and heterocyclic groups which may be optionally additionally substituted with one or two substituents. The substituents may be halogen (preferably chlorine or fluorine), $C_1$-$C_4$ alkyl (preferably methyl, ethyl or isopropyl), cyano, nitro, hydroxy, $C_1$-$C_4$ alkoxy (preferably methoxy or ethoxy), thiol, $C_1$-$C_4$ alkylthio (preferably methylthio or ethylthio), amino, N-($C_1$-$C_4$) alkylamino (preferably N-methylamino or N-ethylamino), N,N-di($C_1$-$C_4$-alkyl)-amino (preferably N,N-dimethylamino or N,N-diethylamino), sulfonyl, $C_1$-$C_4$ alkylsulfonyl (preferably methylsulfonyl or ethylsulfonyl), sulfinyl, $C_1$-$C_4$ alkylsulfinyl (preferably methylsulfinyl).

When X has the meaning of $NR^a$ and $R^a$ has the meaning of a protecting group, then $R^a$ relates to groups such as alkyl (preferably methyl or ethyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).

When $R^2$ and $R^3$ together with N have the meaning of heteroaryl or heterocycle, this means that such heteroaryls or heterocycles have at least one carbon atom replaced by a nitrogen atom, through which the groups are linked to the rest of the molecule. Examples of such groups are morpholine-4-yl, piperidine-1-yl, pyrrolidine-1-yl, imidazole-1-yl or piperazine-1-yl.

The term "pharmaceutically suitable salts" relates to salts of the compounds of the formula I and include e.g. salts with $C_1$-$C_4$ alkylhalides (preferably methyl bromide, methyl chloride) (quaternary ammonium salts), with inorganic acids (hydrochloric, hydrobromic, phosphoric, metaphosphoric, nitric or sulfuric acids) or with organic acids (tartaric, acetic, citric, maleic, lactic, fumaric, benzoic, succinic, methane sulfonic or p-toluene sulfonic acids).

Some compounds of the formula I may form salts with organic or inorganic acids or bases and these are also included in the present invention.

Solvates (most frequently hydrates) which may be formed by the compounds of the formula I or salts thereof are also an object of the present invention.

Depending upon the nature of particular substituents, the compounds of the formula I may have geometric isomers and one or more chiral centres so that there can exist enantiomers or diastereoisomers. The present invention also relates to such isomers and mixtures thereof, including racemates.

The present invention also relates to all possible tautomeric forms of particular compounds of the formula I.

A further object of the present invention relates to the preparation of compounds of the formula I according to processes comprising:

a) a cyclization of α-bromoketones of the formula III:

III

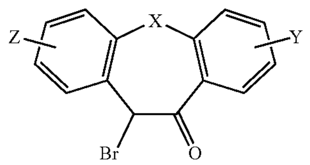

with the compounds of the formula IV:

IV

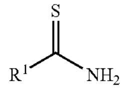

b) for the compounds of the formula I, wherein $Q_1$ has the meaning of —O—, a reaction of alcohols of the formula V:

V

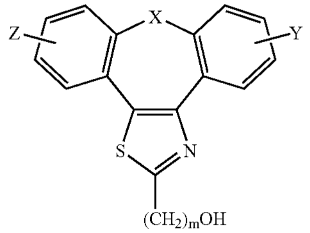

with the compounds of the formula VI:

VI

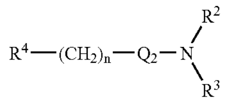

wherein $R^4$ has the meaning of a leaving group;

c) for the compounds of the formula I, wherein $Q_1$ has the meaning of —O—, —NH—, —S— or —C≡C—, a reaction of the compounds of the formula Va:

Va

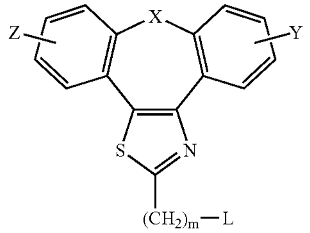

wherein L has a meaning of a leaving group, with the compounds of the formula VIa:

VIa

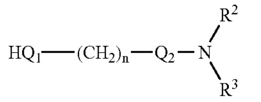

d) for the compounds of the formula I, wherein $Q_1$ has the meaning of a heteroatom —O—, —NH— ili —S—, a reaction of the compounds of the formula Vb:

Vb

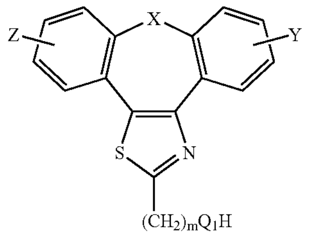

with the compounds of the formula VI, wherein $R^4$ has the meaning of a leaving group;

e) for the compounds of the formula I, wherein $Q_1$ has the meaning of —C═C—, a reaction of the compounds of the formula Va, wherein $Q_1$ has the meaning of carbonyl, with phosphorous ylides.

Preparation Methods:

a) Cyclization of α-bromoketones of the formula III and thioamides of the formula IV is carried out by methods disclosed for the preparation of analogous compounds (Teitei, *Aust. J. Chem.,* 1980, 33:605-611). The reaction is carried out in an appropriate solvent such as e.g. ethanol, propanol, isopropanol, N,N-dimethylformamide, N,N-dimethylacetamide, toluene or xylene at an elevated temperature (preferably from 50° C. to 150° C.). The formed tetracyclic products may be isolated by column chromatography or recrystallization from an appropriate solvent.

The starting compounds for this reaction are already known or they are prepared by methods described for the preparation of analogous compounds: for α-bromoketones of the formula III in e.g. U.S. Pat. Nos. 3,711,489 or 4,198,421, or for thioamides of the formula IV, in e.g. Kavtunenko V. A. et al., *Ukr. Khim. Zh.,* 1983, 49:975-978. The so obtained compounds may be purified, isolated and characterized or may be subjected to a further cyclisation reaction without isolation.

b) The compounds of the formula I according to the present process may be prepared by a reaction of alcohols of the formula V and of compounds of the formula VI, wherein $R^4$ has the meaning of a leaving group, which may be a halogen atom (most frequently bromine, iodine or chlorine) or sulfonyloxy group (most frequently trifluoromethylsulfonyloxy or p-toluenesulfonyloxy). The condensation reaction may be carried out according to methods disclosed for the preparation of analogous compounds (Menozzi G et al., *J. Heterocyclic Chem.,* 1997, 34:963-968 or WO 01/87890). The reaction is carried out at a temperature from 20° C. to 100° C. during 1 to 24 hours in a two-phase system (preferably with 50% NaOH/toluene) in the presence of a phase transfer catalyst (preferably benzyl triethyl ammonium chloride, benzyl triethyl ammonium bromide, cetyl trimethyl bromide). After the treatment of the reaction mixture, the products formed are isolated by recrystallization or chromatography on a silica gel column.

The starting compounds, alcohols of the formula V, may be prepared from the compounds of the formula I, wherein $R^1$ has the meaning of an appropriate functional group. So, the alcohols of the formula V may be obtained by the reduction of an alkanoyl group (e.g. formyl) or alkyloxycarbonyl group (e.g. methyloxycarbonyl or ethyloxycarbonyl) by the use of metal hydrides such as lithium aluminum hydride or sodium borohydride. Further, the alcohols of the formula IV may be prepared by hydrolysis of the corresponding esters (in alkaline or acidic mediums).

The starting compounds of the formula VI are already known or are prepared according to methods disclosed for the preparation of analogous compounds.

c) Compounds of the formula I may be prepared according to the present process by reacting compounds of the formula Va, wherein L has the meaning of a leaving group as defined earlier for $R^4$, and compounds of the formula VIa, wherein $Q_1$ has the meaning of oxygen, nitrogen, sulfur or —C═C—. The most suitable condensation reactions are reactions of nucleophilic substitution on a saturated carbon atom as disclosed in the literature.

The starting compounds of the formula Va (most frequently halides) may be obtained by halogenation (e.g. bromination or chlorination) of compounds of the formula V with the usual halogenating agents (e.g. hydrobromic acid, $PBr_3$, $SOCl_2$ or $PCl_5$) by processes as disclosed in the literature. The obtained compounds may be isolated or may be used without isolation as suitable intermediates for the preparation of the compounds of the formula I.

The starting compounds of the formula VIa are already known or are prepared according to methods disclosed for the preparation of analogous compounds.

d) The compounds of the formula I, wherein $Q_1$ has the meaning of —O—, —NH— or —S—, may be prepared by the condensation of the compounds of the formula Vb and of compounds of the formula VI, wherein $R^4$ has the meaning of a leaving group as defined earlier. The reaction may be carried out at reaction conditions disclosed in the method b) or at conditions of the nucleophilic substitution reactions disclosed in the literature. The starting alcohols, amines or thiols may be obtained by a reaction of water, ammonia or hydrogen sulfide with compounds Va according to processes disclosed in the literature.

e) The alcohols of the structure V may be oxidized to corresponding compounds of the formula Vb, wherein $Q_1$ has the meaning of carbonyl, which may further, by reaction with corresponding ylide reagents, result in a prolongation of the chain and in the formation of an alkenyl substituent with carbonyl or ester groups as disclosed in HR patent application No. 20000310.

Besides the above-mentioned reactions, the compounds of the formula I may be prepared by transforming other compounds of the formula I and it is to be understood that the present invention also comprises such compounds and processes. A special example of a change of a functional group is the reaction of the aldehyde group with chosen phosphorous ylides resulting in a prolongation of the chain and the formation of an alkenyl substituent with carbonyl or ester groups as disclosed in HR patent application No. 20000310.

These reactions are carried out in solvents such as benzene, toluene or hexane at elevated temperature (most frequently at boiling temperature).

By reacting the compounds of the formula Va with 1-alkyne in an alkaline medium (such as sodium amide in ammonia), compounds of the formula I, wherein $Q_1$ is —C≡C—, are obtained. The reaction conditions of this process are disclosed in the literature. At similar reaction conditions (nucleophilic substitution) various ether, thioether or amine derivatives may be prepared.

The formylation of the compounds of the formula I by processes such as e.g. Vilsmeier acylation or reaction of n-BuLi and N,N-dimethylformamide is a further general example of a transformation. The reaction conditions of these processes are well-known in the literature.

By hydrolysis of the compounds of the formula I having nitrile, amide or ester groups, there may be prepared compounds with a carboxyl group, which are suitable intermediates for the preparation of other compounds with novel functional groups such as e.g. esters, amides, halides, anhydrides, alcohols or amines.

Oxidation or reduction reactions are a further possibility of the change of substituents in the compounds of the formula I. The most frequently used oxidation agents are peroxides (hydrogen peroxide, m-chloroperbenzoic acid or benzoyl peroxide) or permanganate, chromate or perchlorate ions. Thus e.g. by the oxidation of an alcohol group by pyridinyl dichromate or pyridinyl chlorochromate, an aldehyde group is formed, which group may be converted to a carboxyl group by further oxidation. By oxidation of the compounds of the formula I, wherein $R^1$ has the meaning of alkyl, with lead tetraacetate in acetic acid or with N-bromosuccinimide using a catalytic amount of benzoyl peroxide, a corresponding carbonyl derivative is obtained.

By a selective oxidation of alkylthio group, alkylsulfinyl or alkylsulfonyl groups may be prepared.

By the reduction of the compounds with a nitro group, the preparation of amino compounds is made possible. The reaction is carried out under usual conditions of catalytic hydrogenation or electrochemically. By catalytic hydrogenation using palladium on carbon, alkenyl substituents may be converted to alkyl ones or the nitrile group can be converted to aminoalkyl.

Various substituents of the aromatic structure in the compounds of the formula I may be introduced by standard substitution reactions or by usual changes of individual functional groups. Examples of such reactions are aromatic substitutions, alkylations, halogenation, hydroxylation as well as oxidation or reduction of substituents. Reagents and reaction conditions are known from the literature. Thus e.g. by aromatic substitution a nitro group is introduced in the presence of concentrated nitric acid and sulfuric acid. By using acyl halides or alkyl halides, the introduction of an acyl group or an alkyl group is made possible. The reaction is carried out in the presence of Lewis acids such as aluminum- or iron-trichloride in conditions of Friedel-Crafts reaction. By the reduction of the nitro group, an amino group is obtained, which is by a diazotizing reaction converted to a suitable starting group, which may be replaced with one of the following groups: H, CN, OH, Hal.

In order to prevent undesired interaction in chemical reactions, it is often necessary to protect certain groups such as e.g. hydroxy, amino, thio or carboxy. For this purpose a great number of protecting groups may be used [Green T W, Wuts P G H, Protective Groups in Organic Synthesis, John Wiley and Sons, 1999] and the choice, use and elimination thereof are conventional methods in chemical synthesis.

A convenient protection for amino or alkylamino groups are groups such as e.g. alkanoyl (acetyl), alkoxycarbonyl (methoxycarbonyl, ethoxycarbonyl or tert-butoxycarbonyl); arylmethoxycarbonyl (benzyloxycarbonyl), aroyl (benzoyl) or alkylsilyl (trimethylsilyl or trimethylsilylethoxymethyl) groups. The conditions of removing a protecting group depend upon the choice and the characteristics of this group. Thus e.g. acyl groups such as alkanoyl, alkoxycarbonyl or aroyl may be eliminated by hydrolysis in the presence of a base (sodium hydroxide or potassium hydroxide), tert-butoxycarbonyl or alkylsilyl (trimethylsilyl) may be eliminated by treatment with a suitable acid (hydrochloric, sulfuric, phosphoric or trifluoroacetic acid), whereas arylmethoxycarbonyl group (benzyloxycarbonyl) may be eliminated by hydrogenation using a catalyst such as palladium on carbon.

Salts of the compounds of the formula I may be prepared by generally known processes such as e.g. by reacting the compounds of the formula I with a corresponding base or acid in an appropriate solvent or solvent mixture e.g. ethers (diethylether) or alcohols (ethanol, propanol or isopropanol).

Another object of the present invention concerns the use of the present compounds in the therapy of inflammatory diseases and conditions, especially of all diseases and conditions induced by excessive TNF-α and IL-1 production.

The inhibitors of production of cytokins or inflammation mediators, which are the object of the present invention, or pharmacologically acceptable salts thereof may be used in the production of drugs for the treatment and prophylaxis of any pathological condition or disease induced by excessive unregulated production of cytokins or inflammation mediators, which drugs should contain an effective dose of said inhibitors. The present invention more specifically relates to an effective dose of TNF-α inhibitor, which may be determined by usual methods.

Further, the present invention relates to a pharmaceutical formulation containing an effective non-toxic dosis of the present compounds as well as pharmaceutically acceptable carriers or solvents.

The preparation of pharmaceutical formulations may include blending, granulating, tabletting and dissolving ingredients. Chemical carriers may be solid or liquid. Solid carriers may be lactose, sucrose, talcum, gelatine, agar, pectin, magnesium stearate, fatty acids etc. Liquid carriers may be syrups, oils such as olive oil, sunflower oil or soya bean oil, water etc. Similarly, the carrier may also contain a component for a sustained release of the active component such as e.g. glyceryl monostearate or glyceryl distearate. Various forms of pharmaceutical formulations may be used. Thus, if a solid carrier is used, these forms may be tablets, hard gelatine capsules, powder or granules that may be administered in capsules per os. The amount of the solid carrier may vary, but it is mainly from 25 mg to 1 g. If a liquid carrier is used, the formulation would be in the form of a syrup, emulsion, soft gelatine capsules, sterile injectable liquids such as ampoules or non-aqueous liquid suspensions.

Compounds according to the present invention may be applied per os, parenterally, locally, intranasally, intrarectally and intravaginally. The parenteral route herein means intravenous, intramuscular and subcutaneous applications. Appropriate formulations of the present compounds may be used in the prophylaxis as well as in the treatment of inflammatory diseases induced by an excessive unregulated production of cytokins or inflammation mediators, primarily TNF-α. They comprise e.g. rheumatoid arthritis, rheumatoid spondylitis, osteoarthritis and other arthritic pathological conditions and diseases, eczemas, psoriasis and other inflammatory skin conditions, inflammatory eye diseases, Crohn's disease, ulcerative colitis and asthma.

The inhibitory action of the present compounds upon TNF-α and IL-1 production was determined by the following in vitro and in vivo experiments:

Determination of TNF-α and IL-1 Secretion in Human Peripheral Blood Mononuclear Cells In Vitro Human peripheral blood mononuclear cells (PBMC) were prepared from heparinized whole blood after separating PBMC on Ficoll-Paque™Plus (Amersham-Pharmacia). To determine the TNF-α level, 3.5-5×$10^4$ cells were cultivated in a total volume of 200 μl for 18 to 24 hours on microtitre plates with a flat bottom (96 wells, Falcon) in RPMI 1640 medium, into which there were added 10% FBS (Fetal Bovine Serum, Biowhittaker) previously inactivated at 54° C./30 min, 100 units/ml of penicillin, 100 mg/ml of streptomycin and 20 mM HEPES (GIBCO). The cells were incubated at 37° C. in an atmosphere with 5% $CO_2$ and 90% humidity. In a negative control the cells were cultivated only in the medium (NC), whereas in a positive control TNF-α secretion was triggered by adding 1 ng/ml of lipopolysaccharides (LPS, *E. coli* serotype 0111:B4, SIGMA) (PC). The effect of the tested substances upon TNF-α secretion was investigated after adding them into cultures of cells stimulated by LPS (TS). The TNF-α level in the cell supernatant was determined by ELISA procedure according to the suggestions of the producer (R&D Systems). The test sensitivity was <3 pg/ml TNF-α. The IL-1 level was determined in an assay under the same conditions and with the same number of cells and the same concentration of stimulus by ELISA procedure (R&D Systems). The percentage of inhibition of TNF-α or IL-1 production was calculated by the equation:

$$\% \text{ inhibition}=[1-(TS-NC)/(PC-NC)]*100.$$

The $IC_{50}$ value was defined as the substance concentration, at which 50% of TNF-α production were inhibited.

Compounds showing $IC_{50}$ with 20 μM or lower concentrations are active.

Determination of TNF-α and IL-1 Secretion in Mouse Peritoneal Macrophages In Vitro In order to obtain peritoneal macrophages, Balb/C mouse strain males, age 8 to 12 weeks, were injected i.p. with 300 μg of zymosan (SIGMA) dissolved in a phosphate buffer (PBS) in a total volume of 0.1 ml/mouse. After 24 hours the mice were euthanized according to the Laboratory Animal Welfare Act. The peritoneal cavity was washed with a sterile physiological solution (5 ml). The obtained peritoneal macrophages were washed twice with a sterile physiological solution and, after the last centrifugation (350 g/10 min), resuspended in RPMI 1640, into which 10% of FBS were added. In order to determine TNF-α secretion, 5×$10^4$ cells/well were cultivated in a total volume of 200 μl for 18 to 24 hours on microtitre plates with a flat bottom (96 wells, Falcon) in RPMI 1640 medium, into which 10% FBS (Fetal Bovine Serum, Biowhittaker) inactivated by heat, 100 units/ml of penicillin, 100 mg/ml of streptomycin, 20 mM HEPES and 50 [M 2-mercaptoethanol (all of GIBCO) were added. The cells were incubated at 37° C. in an atmosphere with 5% $CO_2$ and 90% humidity. In a negative control the cells were cultivated only in a medium (NC), whereas in a positive control the TNF-α secretion was triggered by adding 10 ng/ml of lipopolysaccharides (LPS, *E. coli* serotype 0111:B4, SIGMA) (PC). The effect of the substances upon the TNF-α secretion was investigated after adding them into cultures of cells stimulated with LPS (TS). The TNF-α level in the cell supernatant was determined by ELISA procedure specific for TNF-α or IL-1 (R&D Systems, Biosource). The percentage of inhibition of TNF-α or IL-1 production was calculated by the equation:

$$\% \text{ inhibition}=[1-(TS-NC)/(PC-NC)]*100.$$

The $IC_{50}$ value was defined as the substance concentration, at which 50% of TNF-α production were inhibited.

Compounds showing $IC_{50}$ 10 μM or less are active.

In Vivo Model of LPS-Induced Excessive TNF-α or IL-1 Secretion in Mice

TNF-α or IL-1 secretion in mice was induced according to the already disclosed method (Badger A M et al., *J Pharmac. Env. Therap.,* 1996, 279:1453-1461). Balb/C males, age 8 to 12 weeks, in groups of 6 to 10 animals were used. The animals were treated p.o. either with a solvent only (in negative and in positive controls) or with solutions of substances 30 minutes prior to i.p. treatment with LPS (*E. coli* serotype 0111:B4, Sigma) in a dosis of 1-25 μg/animal. Two hours later the animals were euthanized by means of i.p. Roumpun (Bayer) and Ketanest (Parke-Davis) injection. A blood sample of each animal was taken into a Vacutainer tube (Becton Dickinson) and the plasma was separated according to the producer's instructions. The TNF-α level in the plasma was determined by ELISA procedure (Biosource, R&D Systems) according to the producer's instructions. The test sensitivity was <3 pg/ml TNF-α. The IL-1 level was determined by ELISA procedure (R&D Systems). The percentage of inhibition of TNF-α or IL-1 production was calculated by the equation:

$$\% \text{ inhibition}=[1-(TS-NC)/(PC-NC)]*100.$$

Active are the compounds showing 30% or more inhibition of TNF-α production at a dosis of 10 mg/kg.

Writhing Assay for Analgetic Activity

In this assay pain is induced by the injection of an irritant, most frequently acetic acid, into the peritoneal cavity of mice. Animals react with characteristic writhings, which has given the name of the assay (Collier H O J et al., *Pharmac. Chemother.,* 1968, 32:295-310; Fukawa K et al., *J. Pharmacol. Meth.,* 1980, 4:251-259; Schweizer A et al., *Agents Actions,* 1988, 23:29-31). The assay is convenient for the determination of analgetic activity of compounds. Procedure: male Balb/C mice (Charles River, Italy), age 8 to 12 weeks, were used. A control group received methyl cellulose p.o. 30 minutes prior to i.p. application of acetic acid in a concentration of 0.6%, whereas test groups received standard (acetylsalicylic acid) or test substances in methyl cellulose p.o. 30 minutes prior to i.p. application of 0.6% acetic acid (volume 0.1 ml/10 g). The mice were placed individually under glass funnels and the number of writhings was registered for 20 minutes for each animal. The percentage of writhing inhibition was calculated according to the equation:

% inhibition=(mean value of number of writhings in the control group−number of writhings in the test group)/number of writhings in the control group*100.

Active are the compounds showing such analgetic activity as acetylsalicylic acid or better.

In Vivo Model of LPS-Induced Shock in Mice

Male Balb/C mice (Charles River, Italy), age 8 to 12 weks, were used. LPS isolated from *Serratie marcessans* (Sigma, L-6136) was diluted in sterile physiological solution. The first LPS injection was administered intradermally in a dosis of 4 μg/mouse. 18 to 24 hours later, LPS was administered i.v. in a dosis of 90-200 µg/mouse. A control group received two LPS injections as disclosed above. The test groups received substances p.o. half an hour prior to each LPS application. Survival after 24 hours was observed.

Active are the substances at which the survival at a dosis of 30 mg/kg was 40% or more.

Compounds from Examples (19 and 20) show activity in at least two investigated assays though these results only represent an illustration of the biological activity of the compounds and should not limit the invention in any way.

PREPARATION METHODS WITH EXAMPLES

The present invention is illustrated by the following Examples which are in no way a limitation thereof.

Example 1

2-Phenyl-6-trifluoromethyl-1,8-dithia-3-aza-dibenzo [e,h]azulene (1; Table 1)

A solution of 11-bromo-7-trifluoromethyl-11H-dibenzo [b,f]thiepin-10-one (0.3 mmole) and thiobenzamide (0.6 mmole) in N,N-dimethylformamide (4 ml) was heated for 6 hours at the temperature of 80° C. The solvent was evaporated at reduced pressure to a dry residue and the crude product was purified by extraction on a solid phase (reverse-phase column RP-C18).

According to the above process, by a reaction of 11-bromo-7-trifluoromethyl-11H-dibenzo[b,f]thiepin-10-one and the corresponding thioamide, corresponding azulenes were obtained (Table 1, compounds 2-33).

TABLE 1

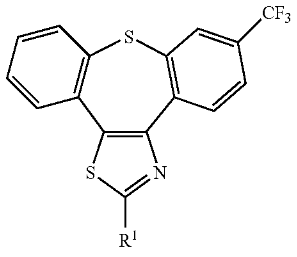

| Comp. | $R^1$ | Mol. formula | MS: m/z $MH^+$ |
|---|---|---|---|
| 1 | 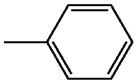 | $C_{22}H_{12}F_3NS_2$ | 412.8 |
| 2 | 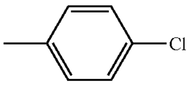 | $C_{22}H_{12}ClF_3NS_2$ | 446.7 |
| 3 | 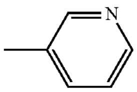 | $C_{21}H_{11}F_3N_2S_2$ | 413.7 |
| 4 | 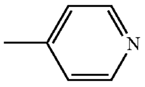 | $C_{21}H_{11}F_3N_2S_2$ | 413.8 |
| 5 | 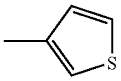 | $C_{20}H_{10}F_3NS_3$ | 418.7 |

TABLE 1-continued

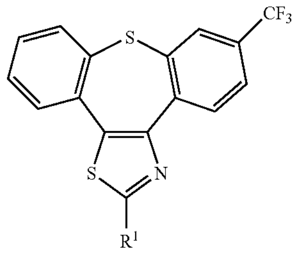

| Comp. | $R^1$ | Mol. formula | MS: m/z $MH^+$ |
|---|---|---|---|
| 6 | 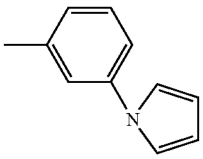 | $C_{26}H_{15}F_3N_2S_2$ | 477.8 |
| 7 | 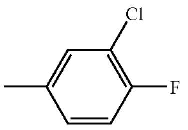 | $C_{22}H_{10}ClF_4S_2$ | 464.1 |
| 8 | 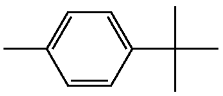 | $C_{26}H_{20}F_3NS_2$ | 468.7 |
| 9 | 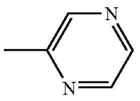 | $C_{20}H_{10}F_3N_3S_2$ | 415.3 |
| 10 | 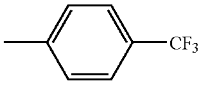 | $C_{23}H_{11}F_6NS_2$ | 480.8 |
| 11 | 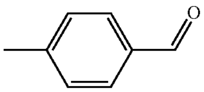 | $C_{23}H_{12}F_3NOS_2$ | 440.2 |
| 12 | 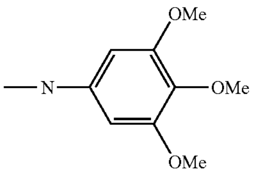 | $C_{25}H_{19}F_3N_2O_3S_2$ | 517.1 |
| 13 | 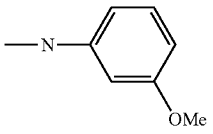 | $C_{23}H_{15}F_3N_2OS_2$ | 457.8 |
| 14 | 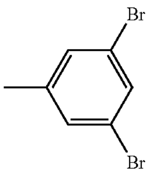 | $C_{22}H_{10}Br_2F_3NS_2$ | 567.9 |

TABLE 1-continued
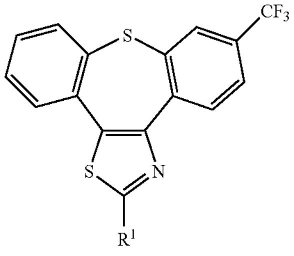
| Comp. | $R^1$ | Mol. formula | MS: m/z $MH^+$ |
|---|---|---|---|
| 15 | 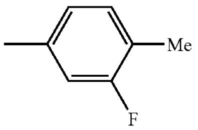 | $C_{23}H_{13}F_4NS_2$ | 444.1 |
| 16 | 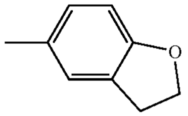 | $C_{24}H_{14}F_3NOS_2$ | 454.1 |
| 17 | 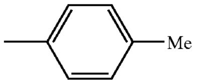 | $C_{23}H_{14}F_3NS_2$ | 426.1 |
| 18 | 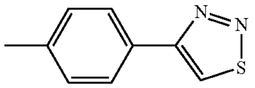 | $C_{24}H_{12}F_3N_3S_3$ | 496.0 |
| 19 | 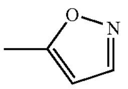 | $C_{19}H_9F_3N_2OS_2$ | 403.1 |
| 20 | 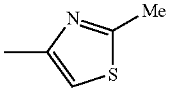 | $C_{20}H_{11}F_3N_2S_3$ | 433.0 |
| 21 | 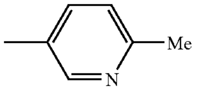 | $C_{22}H_{13}F_3N_2S_2$ | 427.1 |
| 22 | 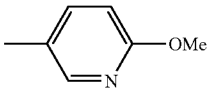 | $C_{22}H_{13}F_3N_2OS_2$ | 443.1 |
| 23 | 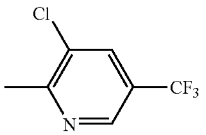 | $C_{22}H_9ClF_6N_2S_2$ | 515.1 |
| 24 | 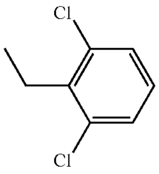 | $C_{23}H_{12}Cl_2F_3NS_2$ | 494.2 |
TABLE 1-continued
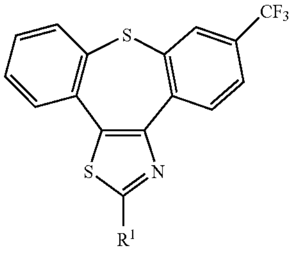
| Comp. | $R^1$ | Mol. formula | MS: m/z $MH^+$ |
|---|---|---|---|
| 25 | 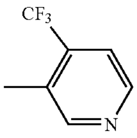 | $C_{22}H_{10}F_6N_2S_2$ | 480.8 |
| 26 | 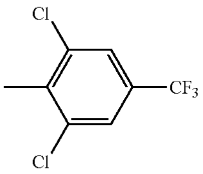 | $C_{23}H_9Cl_2F_6NS_2$ | 548.2 |
| 27 | 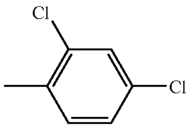 | $C_{22}H_{10}Cl_2F_3NS_2$ | 480.0 |
| 28 | 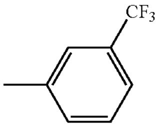 | $C_{23}H_{11}F_6NS_2$ | 480.1 |
| 29 | 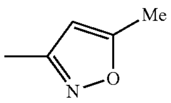 | $C_{20}H_{11}F_3N_2OS_2$ | 417.1 |
| 30 | 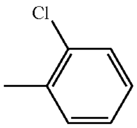 | $C_{22}H_{11}ClF_3NS_2$ | 446.0 |
| 31 | 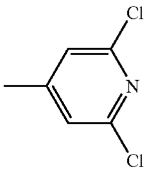 | $C_{21}H_9Cl_2F_3N_2S_2$ | 481.2 |
| 32 | 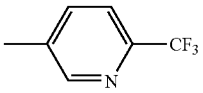 | $C_{22}H_{10}F_6N_2S_2$ | 481.3 |

TABLE 1-continued

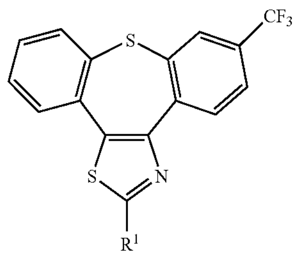

| Comp. | $R^1$ | Mol. formula | MS: m/z $MH^+$ |
|---|---|---|---|
| 33 | 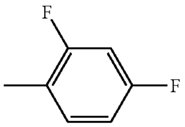 | $C_{22}H_{10}F_5NS_2$ | 448.1 |

Example 2

2-Pyridine-4-yl-6-trifluoromethyl-8-oxa-1-thia-3-aza-dibenzo[e,h]azulene (34; Table 2)

A solution of 11-bromo-7-trifluoromethyl-11H-dibenzo[b,f]oxepin-10-one (0.4 mmole) and pyridinium bromide perbromide (0.45 mmole) in toluene (5 ml) was stirred at room temperature for 4 hours. Then $K_2CO_3$ (50 mg) was added to the reaction mixture. The reaction mixture was stirred for further 10 minutes and filtered. The solvent was evaporated at reduced pressure to a dry residue. To the obtained 11-bromo-7-trifluoromethyl-11H-dibenzo[b,f]oxepin-10-one thioisonicotinamide (0.5 mmole) dissolved in N,N-dimethylformamide (4 ml) was added. The reaction mixture was heated at 80° C. for 6 hours. The solvent was evaporated at reduced pressure to a dry residue and a crude product was purified by extraction on a solid phase (reverse-phase column RP-C18).

According to the above process, by a reaction of thioisonicotinamide and the corresponding bromoketone, corresponding azulenes were obtained (Table 2, compounds 35-49).

TABLE 2

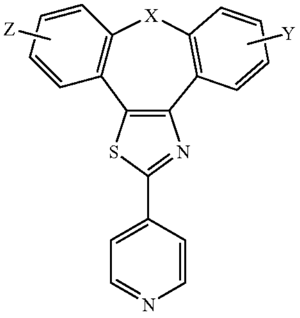

| Comp. | X | Y | Mol. formula | MS: (m/z) $MH^+$ |
|---|---|---|---|---|
| 34 | O | 6-$CF_3$ | $C_{21}H_{11}F_3N_2OS$ | 397.1 |
| 35 | S | 5-Cl; 6-Cl | $C_{20}H_{10}Cl_2N_2S_2$ | 412.8 |
| 36 | $CH_2$ | H | $C_{21}H_{14}N_2S$ | 327.1 |

TABLE 2-continued

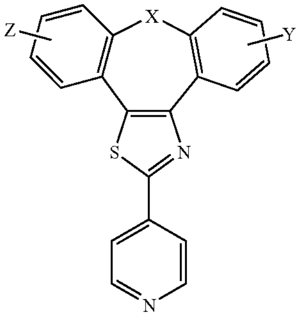

| Comp. | X | Y | Mol. formula | MS: (m/z) $MH^+$ |
|---|---|---|---|---|
| 37 | S | 5-OMe | $C_{21}H_{14}N_2OS_2$ | 375.0 |
| 38 | S | 5-F | $C_{20}H_{11}FN_2S_2$ | 363.1 |
| 39 | S | 7-Cl | $C_{20}H_{11}ClN_2S_2$ | 379.0 |
| 40 | S | 6-Cl | $C_{20}H_{11}ClN_2S_2$ | 379.0 |
| 41 | S | 7-Br | $C_{20}H_{11}BrN_2S_2$ | 345.1 |
| 42 | S | 5-Br | $C_{20}H_{11}BrN_2S_2$ | 423.0 |
| 43 | S | 5-F; 7-Cl | $C_{20}H_{10}ClFN_2S_2$ | 397.0 |
| 44 | S | 5-Me | $C_{21}H_{14}N_2S_2$ | 359.1 |
| 45 | S | 7-Me | $C_{21}H_{14}N_2S_2$ | 359.1 |
| 46 | S | 5-Cl | $C_{20}H_{11}ClN_2S_2$ | 379.1 |
| 47 | S | 6-Me | $C_{21}H_{14}N_2S_2$ | 359.1 |
| 48 | S | 5-F; 6-Cl | $C_{20}H_{10}ClFN_2S_2$ | 397.1 |
| 49 | NCOMe | H | $C_{22}H_{15}N_3OS$ | 369.9 |

In all examples given in the Table 2, Z=H.

Example 3

8-Oxa-1-thia-3-aza-dibenzo[e,h]azulene (50; Table 3)

To a solution of phosphorous (V) sulfide (6.54 mmoles) in formamide (102 mmoles; 4.08 ml), a toluene solution (8.2 ml) of 11-bromo-11H-dibenzo[b,f]oxepin-10-one (4.60 mmoles) was added. The reaction mixture was heated under stirring and refluxing for 4 hours. Then the reaction mixture was neutralized with 10% sodium hydroxide and extracted with chloroform. After purification by chromatography on a silica gel column, a crystalline product was isolated.

According to the above process, starting from the compounds:

11-bromo-8-fluoro-11H-dibenzo[b,f]oxepin-10-one;

11-bromo-8-chloro-11H-dibenzo[b,f]oxepin-10-one;

11-bromo-11H-dibenzo[b,f]thiepin-10-one there were prepared:

5-fluoro-8-oxa-1-thia-3-aza-dibenzo[e,h]azulene;

5-chloro-8-oxa-1-thia-3-aza-dibenzo[e,h]azulene;

1,8-dithia-3-aza-dibenzo[e,h]azulene, (Table 3, compounds 51-53).

Example 4

5-Fluoro-2-methyl-8-oxa-1-thia-3-aza-dibenzo[e,h]azulene (54; Table 3)

To a solution of 11-bromo-8-fluoro-11H-dibenzo[b,f]oxepin-10-one (2.34 mmoles) in dry N,N-dimethylformamide (12 ml), thioacetamide (2.8 mmoles) was added. The reaction mixture was heated under stirring at 90° C. for 3 hours.

Then the solvent was evaporated under reduced pressure and the remaining oily product was dissolved in ethyl acetate and water. After extraction the organic layers were washed with a saturated aqueous $NaHCO_3$ solution, water and a saturated aqueous sodium chloride solution. After purification by chromatography on a silica gel column, a crystalline product was isolated.

According to the above process, starting from the compounds:

11-bromo-8-chloro-11H-dibenzo[b,f]oxepin-10-one;
11-bromo-7-chloro-11H-dibenzo[b,f]thiepin-10-one;
11-bromo-7-trifluoromethyl-11H-dibenzo[b,f]thiepin-10-one;
7,11-dibromo-11H-dibenzo[b,f]thiepin-10-one;
8,11-dibromo-11H-dibenzo[b,f]thiepin-10-one;
11-bromo-8-chloro-11H-dibenzo[b,f]thiepin-10-one;
11-bromo-11H-dibenzo[b,f]thiepin-10-one;
11-bromo-11H-dibenzo[b,f]oxepin-10-one there were prepared:

5-chloro-2-methyl-8-oxa-1-thia-3-aza-dibenzo[e,h]azulene;
6-chloro-2-methyl-1,8-dithia-3-aza-dibenzo[e,h]azulene;
2-methyl-6-trifluoromethyl-1,8-dithia-3-aza-dibenzo[e,h]azulene;
6-bromo-2-methyl-1,8-dithia-3-aza-dibenzo[e,h]azulene;
5-bromo-2-methyl-1,8-dithia-3-aza-dibenzo[e,h]azulene;
5-chloro-2-methyl-1,8-dithia-3-aza-dibenzo[e,h]azulene;
2-methyl-1,8-dithia-3-aza-dibenzo[e,h]azulene;
2-methyl-8-oxa-1-thia-3-aza-dibenzo[e,h]azulene,
(Table 3, compounds 55-62).

Example 5

(6-Chloro-1,8-dithia-3-aza-dibenzo[e,h]azulene-2-yl)-acetonitrile (63; Table 3)

To a solution of 11-bromo-7-chloro-11H-dibenzo[b,f]thiepin-10-one (3.75 mmoles) in absolute ethanol (19 ml), 2-cyanothioacetamide (5.63 mmoles) was added. The reaction mixture was heated under stirring and refluxing for 8 hours. Then the solvent was evaporated under reduced pressure and the remaining dry residue was dissolved in water and ethyl acetate. After extraction the organic layers were washed with a saturated aqueous $NaHCO_3$ solution, water and a saturated aqueous sodium chloride solution. After purification by chromatography on a silica gel column a crystalline product was isolated.

Example 6

6-Trifluoromethyl-1,8-dithia-3-aza-dibenzo[e,h]azulene-2-carboxylic acid ethyl ester (70; Table 3)

To a solution of 11-bromo-7-trifluoromethyl-11H-dibenzo[b,f]thiepin-10-one (1.37 mmoles) in dry N,N-dimethylformamide (7 ml), ethyl thiooxamate (1.5 mmoles) was added. The reaction mixture was heated under stirring at 80° C. for 3 hours. Then the solvent was evaporated under reduced pressure and the remaining oily product was dissolved in ethyl acetate and water. After extraction the organic layer was washed with a saturated aqueous $NaHCO_3$ solution, water and a saturated aqueous sodium chloride solution. After purification by chromatography on a silica gel column a crystalline product was isolated.

According to the above process, starting from 11-bromo-8-fluoro-11H-dibenzo[b,f]thiepin-10-one there was prepared 5-fluoro-1,8-dithia-3-aza-dibenzo[e,h]azulene-2-carboxylic acid ethyl ester (71; Table 3).

Example 7

8-Oxa-1-thia-3-aza-dibenzo[e,h]azulene-2-carbaldehyde (64; Table 3)

To a solution of the compound 50 (1.99 mmoles) in dry tetrahydrofurane (5 ml), cooled to −78° C., n-BuLi (5.77 mmoles) was added. After 15 minutes N,N-dimethylformamide (4.98 mmoles; 0.38 ml) was added to the reaction mixture. The reaction mixture was stirred at room temperature for 1 hour, then water was added and it was extracted with ethyl acetate. The combined organic extracts were evaporated under reduced pressure and the remaining dry residue was purified by chromatography on a silica gel column.

According to the above process, starting from the compounds 51-53, there were prepared the aldehydes:

5-fluoro-8-oxa-1-thia-3-aza-dibenzo[e,h]azulene-2-carbaldehyde;
5-chloro-8-oxa-1-thia-3-aza-dibenzo[e,h]azulene-2-carbaldehyde;
1,8-dithia-3-aza-dibenzo[e,h]azulene-2-carbaldehyde;

(compounds 65-67; Table 3).

Example 8

(6-Chloro-1,8-dithia-3-aza-dibenzo[e,h]azulene-2-yl)-acetic acid ethyl ester (69; Table 3)

To a solution of the compound 63 (0.53 mmole) in ethanol (2 ml) concentrated sulfuric acid (0.5 ml) was added dropwise under stirring. The reaction mixture was heated under refluxing for 4 hours and then cooled to room temperature and poured into water (5 ml). The reaction mixture was extracted with ethyl acetate. The combined organic extracts were evaporated under reduced pressure, whereat an oily product remained.

Example 9

5-Fluoro-8-oxa-1-thia-3-aza-dibenzo[e,h]azulene-2-yl-acetic acid methyl ester (72; Table 3)

To a solution of the compound 54 (0.21 mmole) in acetic acid (5 ml), lead (IV) acetate was added under stirring. The reaction mixture was heated under refluxing for 8 hours. Then acetic acid was evaporated under reduced pressure and the remaining dry residue was dissolved in water and extracted with ethyl acetate. The combined extracts were washed with water and a saturated aqueous sodium chloride solution and evaporated under reduced pressure. After purification by chromatography on a silica gel column a crystalline product was isolated.

According to the above process, starting from the compound 55, there was prepared 5-chloro-8-oxa-1-thia-3-aza-dibenzo[e,h]azulene-2-yl-acetic acid methyl ester (73; Table 3).

TABLE 3

I

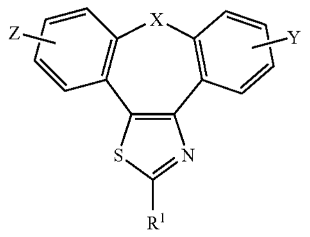

| Comp. | X | Y | $R^1$ | MS (m/z) $MH^+$ | $^1H$ NMR (ppm, $CDCl_3$) |
|---|---|---|---|---|---|
| 50 | O | H | H | 251.9 | 7.16–7.98 (m, 8H); 8.86 (s, 1H) |
| 51 | O | 5-F | H | 270.0 | 7.01–7.70 (m, 7H); 8.96 (s, 1H) |
| 52 | O | 5-Cl | H | — | 7.22–7.99 (m, 7H); 8.94 (s, 1H) |
| 53 | S | H | H | 268.0 | 7.02–8.98 (m, 8H); 9.13 (s, 1H) |
| 54 | O | 5-F | $CH_3$ | — | 2.84 (s, 3H); 7.20–8.33 (m, 7H) |
| 55 | O | 5-Cl | $CH_3$ | — | 2.89 (s, 3H); 7.20–8.33 (m, 7H) |
| 56 | S | 6-Cl | $CH_3$ | 316.2 | — |
| 57 | S | 6-$CF_3$ | $CH_3$ | 350.0 | — |
| 58 | S | 6-Br | $CH_3$ | 362.2 | — |
| 59 | S | 5-Br | $CH_3$ | 361.0 | — |
| 60 | S | 5-Cl | $CH_3$ | 316.0 | — |
| 61 | S | H | $CH_3$ | 282.2 | — |
| 62 | O | H | $CH_3$ | — | 7.18–8.98 (m, 8H); 2.84 (s, 3H) |
| 63 | S | 6-Cl | $CH_2CN$ | 341.2 | 3.45 (s, 2H); 7.26–7.82 (m, 7H) |
| 64 | O | H | CHO | 280.3 | 6.99–7.99 (m, 8H); 10.05 (s, 1H) |
| 65 | O | 5-F | CHO | — | 7.20–7.99 (m, 7H); 10.05 (s, 1H) |
| 66 | O | 5-Cl | CHO | — | 7.14–7.99 (m, 7H); 9.97 (s, 1H) |
| 67 | S | H | CHO | 296.1 | 7.21–7.96 (m, 8H); 10.07 (s, 1H) |
| 68 | S | 6-Cl | $CH{=}CH_2$ | 328.1 | — |
| 69 | S | 6-Cl | $CH_2CO_2C_2H_5$ | 388.1 | — |
| 70 | S | 6-$CF_3$ | $CO_2C_2H_5$ | 407.9 | — |
| 71 | S | 5-F | $CO_2C_2H_5$ | 357.9 | — |
| 72 | O | 5-F | $CH_2OCOCH_3$ | 342.0 | — |
| 73 | O | 5-Cl | $CH_2OCOCH_3$ | 358.0 | — |

In all Examples given in the Table 3, Z=H.

Example 10

(8-Oxa-1-thia-3-aza-dibenzo[e,h]azulene-2-yl)-methanol (74; Table 4)

To a solution of the compound 64 (0.60 mmole) in methanol (10 ml), $NaBH_4$ (0.90 mmole) was added under stirring at room temperature. The reaction mixture was stirred for 15 minutes. After the complete quantity of the aldehyde had reacted, the reaction mixture was neutralized with acetic acid and the solvent was evaporated under reduced pressure. The obtained dry residue was dissolved in a saturated aqueous $NaHCO_3$ solution and extracted with ethyl acetate. The organic extract was washed with water and a saturated aqueous sodium chloride solution. The solvent was evaporated under reduced pressure and then the crude product was recrystallized from a mixture of ethyl acetate and hexane.

According to the above process, starting from the aldehydes 65-67, there were prepared the alcohols:

(5-fluoro-8-oxa-1-thia-3-aza-dibenzo[e,h]azulene-2-yl)-methanol;

(5-chloro-8-oxa-1-thia-3-aza-dibenzo[e,h]azulene-2-yl)-methanol;

(1,8-dithia-3-aza-dibenzo[e,h]azulene-2-yl)-methanol (Table 4, compounds 75-77).

Example 11

2-(6-Chloro-1,8-dithia-3-aza-dibenzo[e,h]azulene-2-yl)-ethanol (78; Table 4)

To a suspension of $LiAlH_4$ in dry ether (2 mmoles/5 ml of dry ether), an ether solution of the ester 69 (1 mmol/5 ml) was added dropwise. The reaction mixture was stirred at room temperature for 2 hours. After the complete quantity of the ester had reacted, the excess of $LiAlH_4$ was decomposed by the addition of diethyl ether and water. The formed white precipitate was filtered off and, after drying on anhydrous sodium sulfate, the filtrate was evaporated under reduced pressure. The crude product was purified by chromatography on a silica gel column.

Example 12

(6-Trifluoromethyl-1,8-dithia-3-aza-dibenzo[e,h]azulene-2-yl)-methanol (79; Table 4)

To a solution of the compound 70 (0.60 mmole) in methanol (10 ml), $NaBH_4$ (0.90 mmole) was added under stirring at room temperature. The reaction mixture was stirred for 15 minutes. After the complete quantity of the ester had reacted, the reaction mixture was neutralized with acetic acid and the solvent was evaporated under reduced pressure. To the obtained dry residue a saturated aqueous $NaHCO_3$ solution was added and it was extracted with ethyl acetate. The organic extract was washed with water and a saturated aqueous sodium chloride solution. The solvent was evaporated under reduced pressure and the crude product was recrystallized from a mixture of ethyl acetate and hexane and a pure product was obtained.

According to the above process, starting from the ester 71, there was prepared (5-fluoro-1,8-dithia-3-aza-dibenzo[e,h]azulene-2-yl)-methanol (80; Table 4).

Example 13

(5-Fluoro-8-oxa-1-thia-3-aza-dibenzo[e,h]azulene-2-yl)-methanol (75; Table 4)

To a solution of the ester 72 (1 mmole) in ethanol (36 ml), potassium hydroxide (2.5 mmoles) and water (4 ml) were added. The reaction mixture was stirred and heated under refluxing for 1 hour. After the complete quantity of the ester had reacted, ethanol was evaporated under reduced pressure. The obtained dry residue was dissolved in water and extracted with ethyl acetate. The organic extracts were washed with a saturated aqueous $NaHCO_3$ solution, water and a saturated aqueous sodium chloride solution. The obtained dry residue was purified by chromatography on a silica gel column.

According to the above process, starting from the ester 73, there was prepared the alcohol, (5-chloro-8-oxa-1-thia-3-aza-dibenzo[e,h]azulene-2-yl)-methanol (76; Table 4).

TABLE 4

V

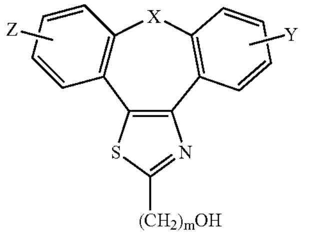

| Comp. | m | X | Y | MS (m/z) MH+ | $^1H$ NMR (ppm, $CDCl_3$) |
|---|---|---|---|---|---|
| 74 | 1 | O | H | 282.1 | 5.06 (s, 2H), 7.17–7.92 (m, 8H) |
| 75 | 1 | O | 5-F | 297.9 | 5.12 (s, 2H), 7.07–7.68 (m, 7H) |
| 76 | 1 | O | 5-Cl | 314.0 | — |
| 77 | 1 | S | H | 298.6 | — |
| 78 | 2 | S | 6-Cl | 344.0 | — |
| 79 | 1 | S | $6-CF_3$ | 366.0 | — |
| 80 | 1 | S | 5-F | 315.9 | — |

In all Examples given in the Table 4, Z=H.

Example 14 a) Dimethyl-[2-(8-oxa-1-thia-3-aza-dibenzo[e,h]azulene-2-ylmethoxy)-ethyl]-amine (I; X=O, Y=Z=H, $R^1=(CH_3)_2N(CH_2)_2OCH_2$)

To solution of 2-dimethylaminoethylchloride-hydrochloride (14 mmoles) in 50% sodium hydroxide (5 ml), benzyltriethylammonium chloride (0.44 mmole) and a solution of the alcohol 74 (1 mmole) in toluene (3 ml) were added. The reaction mixture was heated under refluxing und vigorous stirring for 4 hours. Then it was cooled to room temperature, diluted with water and extracted with dichloromethane. After purification by chromatography on a silica gel column an oily product was isolated.

$^1H$ NMR (ppm, $CDCl_3$): 2.58 (s, 6H); 2.92-2.95 (t, 2H); 3.92-3.98 (t, 2H); 4.91(s, 2H); 7.15-7.90 (m, 8H); MS (m/z): 353.3 ($MH^+$).

b) Dimethyl-[3-(8-oxa-1-thia-3-aza-dibenzo[e,h]azulene-2-ylmethoxy)-propyl]-amine (I; X=O, Y=Z=H, $R^1=(CH_3)_2N(CH_2)_3OCH_2$)

By reacting the alcohol 74 (1.5 mmoles) and 3-dimethylaminopropylchloride-hydrochloride (21 mmoles) an oily product was obtained.

$^1H$ NMR (ppm, $CDCl_3$): 2.23 (m, 2H); 2.83-2.85 (d, 6H); 3.15-3.25 (m, 2H); 3.72-3.84 (t, 2H); 4.90 (s, 2H): 7.18-7.91(m, 8H); MS (m/z): 367.3 ($MH^+$).

c) 3-(8-Oxa-1-thia-3-aza-dibenzo[e, h]azulene-2-ylmethoxy)-propyl]-amine (I; X=O, Y=Z=H, $R^1=H_2N(CH_2)_3OCH_2$)

By reacting the alcohol 74 (1.5 mmol) and 3-aminopropylchloride-hydrochloride (21 mmoles) an oily product was obtained.

MS (m/z): 339.1 ($MH^+$).

Example 15 a) [2-(5-Fluoro-8-oxa-1-thia-3-aza-dibenzo[e,h]azulene-2-ylmethoxy)-ethyl]-dimethylamine (I; X=O, Y=5-F, Z=H, $R^1=(CH_3)_2N(CH_2)_2OCH_2$)

To a solution of 2-dimethylaminoethylchloride-hydrochloride (21 mmoles) in 50% sodium hydroxide (5 ml), benzyltriethylammonium chloride (0.25 g) and a solution of the alcohol 75 (1.5 mmoles) in toluene (5 ml) were added. The reaction mixture was heated under refluxing and vigorous stirring for 3 hours. Then it was cooled to room temperature, diluted with water and extracted with dichloromethane. After purification by chromatography on a silica gel column an oily product was isolated.

$^1H$ NMR (ppm, $CDCl_3$): 2.67 (s, 6H); 2.92-3.03 (m, 2H); 4.02-4.10 (m, 2H); 4.91 (s, 2H); 7.02-7.59 (m, 7H); MS (m/z): 371.3 ($MH^+$).

b) [3-(5-Fluoro-8-oxa-1-thia-3-aza-dibenzo[e,h]azulene-2-ylmethoxy)-propyl]-dimethylamine (I; X=O, Y=5-F, Z=H, $R^1=(CH_3)_2N(CH_2)_3OCH_2$)

By reacting the alcohol 75 (1.5 mmoles) and 3-dimethylaminopropylchloride-hydrochloride (21 mmoles) an oily product was obtained.

MS (m/z): 385.0 ($MH^+$).

Example 16 a) [2-(5-Chloro-8-oxa-1-thia-3-aza-dibenzo[e,h]azulene-2-ylmethoxy)-ethyl]-dimethylamine (I; X=O, Y=5-Cl, Z=H, $R^1=(CH_3)_2N(CH_2)_2OCH_2$)

To a solution of 2-dimethylaminoethylchloride-hydrochloride (21 mmoles) in 50% sodium hydroxide (5 ml), benzyltriethylammonium chloride (0.25 g) and a solution of the alcohol 76 (1.5 mmoles) in toluene (4 ml) were added. The reaction mixture was heated under refluxing and vigorous stirring for 3 hours. Then it was cooled to room temperature, diluted with water and extracted with dichlo romethane. After purification by chromatography on a silica gel column an oily product was isolated.

MS (m/z): 386.9 ($MH^+$).

b) [3-(5-Chloro-8-oxa-1-thia-3-aza-dibenzo[e, h]azulene-2-ylmethoxy)-propyl]-dimethylamine (I; X=O, Y=5-Cl, Z=H, $R^1$=$(CH_3)_2N(CH_2)_3OCH_2$)

By reacting the alcohol 76 (1.5 mmoles) and 3-dimethylaminopropylchloride-hydrochloride (21 mmoles) an oily product was obtained.

$^1$H NMR (ppm, $CDCl_3$): 1.87-2.00 (m, 2H); 2.32 (s, 6H); 2.39-2.54 (t, 2H); 3.57-3.87 (t, 2H); 4.86 (s, 2H); 7.17-7.88 (m, 7H); MS (m/z): 401.0 ($MH^+$).

Example 17 a) [2-(1,8-Dithia-3-aza-dibenzo[e, h]azulene-2-ylmethoxy)-ethyl]-dimethylamine (I; X=S, Y=Z=H, $R^1$=$(CH_3)_2N(CH_2)_2OCH_2$)

To a solution of 2-dimethylaminoethylchloride-hydrochloride (21 mmoles) in 50% sodium hydroxide (5 ml), benzyltriethylammonium chloride (0.25 g) and a solution of the alcohol 77 (1.5 mmoles) in toluene (3 ml) were added. The reaction mixture was heated under refluxing and vigorous stirring for 3 hours. Then it was cooled to room temperature, diluted with water and extracted with dichloromethane. After purification by chromatography on a silica gel column, an oily product was isolated.

MS (m/z): 369.2 ($MH^+$).

b) [3-(1,8-Dithia-3-aza-dibenzo[e,h]azulene-2-ylmethoxy)-propyl]-dimethylamine (I; X=S, Y=Z=H, $R^1$=$(CH_3)_2N(CH_2)_3OCH_2$)

By reacting the alcohol 77 (1.5 mmoles) and 3-dimethylaminopropychloride-hydrochloride (21 mmoles) an oily product was obtained.

$^1$H NMR (ppm, $CDCl_3$): 2.27-2.32 (m, 2H); 2.83-2.84 (d, 6H); 3.15-3.25 (t, 2H); 3.83-3.87 (t, 2H); 4.99 (s, 2H); 7.08-7.55 (m, 8H); MS (m/z): 383.1 ($MH^+$).

Example 18

{3-[2-(6-Chloro-1,8-dithia-3-aza-dibenzo[e,h]azulene-2-yl)-ethoxy]-propyl}-dimethylamine (I; X=S, Y=6-Cl, Z=H, $R^1$=$(CH_3)_2N(CH_2)_3O(CH_2)_2$)

6-Chloro-2-vinyl-1,8-dithia-3-aza-dibenzo[e,h]azulene (I; X=S, Y=6-Cl, Z=H, $R^1$=($CH_2$=CH)

To a solution of 3-dimethylaminopropylchloride-hydrochloride (14 mmoles) in 50% sodium hydroxide (5 ml), benzyltriethylammonium chloride (0.25 g) and a solution of the alcohol 78 (1 mmol) in toluene (2 ml) were added. The reaction mixture was heated under refluxing and vigorous stirring for 3 hours. Then it was cooled to room temperature, diluted with water and extracted with dichloromethane. After purification by chromatography on a silica gel column an oily product, {3-[2-(6-chloro-1,8-dithia-3-aza-dibenzo[e, h]azulene-2-yl)-ethoxy]-propyl}-dimethylamine;

MS (m/z): 431.3 ($MH^+$), and crystalline 6-chloro-2-vinyl-1,8-dithia-3-aza-dibenzo[e, h]azulene (68; Table 3); were isolated.

Example 19 a) Dimethyl-[2-(6-trifluoromethyl-1,8-dithia-3-aza-dibenzo[e,h]azulene-2-ylmethoxy)-ethyl]-amine (I; X=S, Y=6-$CF_3$, Z=H, $R^1$=$(CH_3)_2N(CH_2)_2OCH_2$)

To a solution of 2-dimethylaminoethylchloride-hydrochloride (12 mmoles) in 50% sodium hydroxide (5 ml), benzyltriethylammonium chloride (0.044 mmole) and a solution of the alcohol 79 (1.1 mmole) in toluene (4 ml) were added. The reaction mixture was heated under refluxing and vigorous stirring for 3 hours. Then it was cooled to room temperature, diluted with water and extracted with dichloromethane. After purification by chromatography on a silica gel column, an oily product was isolated.

MS (m/z): 437.1 ($MH^+$).

b) Dimethyl-[3-(6-trifluoromethyl-1,8-dithia-3-aza-dibenzo[e,h]azulene-2-ylmethoxy)-propyl]-amine (I; X=S, Y=6-$CF_3$, Z=H, $R^1$=$(CH_3)_2N(CH_2)_3OCH_2$)

By reacting the alcohol 79 (0.84 mmole) and 3-dimethylaminopropylchloride-hydrochloride (0.019 mole) an oily product was obtained.

MS (m/z): 451 ($MH^+$).

Example 20 a) [2-(5-Fluoro-1,8-dithia-3-aza-dibenzo[e,h]azulene-2-ylmethoxy)-ethyl]-dimethylamine (I; X=S, Y=5-F, Z=H, $R^1$=$(CH_3)_2N(CH_2)_2OCH_2$)

To a solution of 2-dimethylaminoethylchloride-hydrochloride (12 mmoles) in 50% sodium hydroxide (5 ml), benzyltriethylammonium chloride (0.65 mmole) and a solution of the alcohol 80 (1.1 mmole) in toluene (5 ml) were added. The reaction mixture was heated under vigorous stirring and refluxing for 3 hours. Then it was cooled to room temperature, diluted with water and extracted with dichloromethane. After purification by chromatography on a silica gel column, an oily product was isolated.

MS (m/z): 387.1 ($MH^+$).

b) [3-(5-Fluoro-1,8-dithia-3-aza-dibenzo[e,h]azulene-2-ylmethoxy)-propyl]-dimethylamine (I; X=S, Y=5-F, Z=H, $R^1$=$(CH_3)_2N(CH_2)_3OCH_2$)

By reacting the alcohol 80 (0.84 mmole) and 3-dimethylaminopropylchloride-hydrochloride (19 mmoles) an oily product was obtained.

MS (m/z): 401.0 ($MH^+$).

Preparation of Starting Compounds

Preparation of α-bromoketones

11-Bromo-11H-dibenzo[b,f]oxepin-10-one (III; X=O, Y=Z=H)

To a solution of 11H-dibenzo[b,f]oxepin-10-one (6.8 mmoles) in 6 ml of acetic acid, previously heated to 55-60° C., a solution of bromine (7.5 mmoles, 0.382 ml) in 3 ml of acetic acid was added dropwise under stirring. The reaction mixture was stirred at the temperature of 60° C. for 1.5 hours and then purged by a flow of argon, whereby hydrogen bromide was formed. After cooling to room temperature, the reaction mixture was poured into water and extracted with dichloromethane. The obtained precipitate was recrystallized from ethanol and the obtained crystals were filtered off.

According to the above process, starting from:

8-fluoro-11H-dibenzo[b,f]oxepin-10-one;

8-chloro-11H-dibenzo[b,f]oxepin-10-one;

11H-dibenzo[b,f]thiepin-10-one;

7-chloro-11H-dibenzo[b,f]thiepin-10-one;

7-trifluoromethyl-11H-dibenzo[b,f]thiepin-10-one;

8-fluoro-11H-dibenzo[b,f]thiepin-10-one;

8-chloro-11H-dibenzo[b,f]thiepin-10-one;

7-bromo-11H-dibenzo[b,f]thiepin-10-one;

8-bromo-11H-dibenzo[b,f]thiepin-10-one, 7,8-dichloro-11H-dibenzo[b,f]thiepin-10-one;

8-methoxy-11H-dibenzo[b,f]thiepin-10-one there were prepared the compounds:

11-bromo-8-fluoro-11H-dibenzo[b,f]oxepin-10-one (III; X=O, Y=8-F, Z=H);

11-bromo-8-chloro-11H-dibenzo[b,f]oxepin-10-one (III; X=O, Y=8-Cl, Z=H);

11-bromo-11H-dibenzo[b,f]thiepin-10-one (III; X=S, Y=Z=H);

11-bromo-7-chloro-11H-dibenzo[b,f]thiepin-10-one (III; X=S, Y=7-Cl, Z=H);

11-bromo-7-trifluoromethyl-11H-dibenzo[b,f]thiepin-10-one (III; X=S, Y=7-$CF_3$, Z=H);

11-bromo-8-fluoro-11H-dibenzo[b,f]thiepin-10-one (III; X=S, Y=8-F, Z=H);

11-bromo-8-chloro-11H-dibenzo[b,f]thiepin-10-one (III; X=S, Y=8-Cl, Z=H);

7,11-dibromo-11H-dibenzo[b,f]thiepin-10-one (III; X=S, Y=7-Br, Z=H);

8,11-dibromo-11H-dibenzo[b,f]thiepin-10-one (III; X=O, Y=8-Br, Z=H); 11-bromo-7,8-dichloro-11H-dibenzo[b,f]thiepin-10-one (III; X=S, Y=7-Cl and 8-Cl, Z=H);

11-bromo-8-methoxy-11H-dibenzo[b,f]thiepin-10-one (III; X=S, Y=5—$OCH_3$, Z=H).

The characteristics of the obtained products of the formula III are shown in the Table 5.

TABLE 5

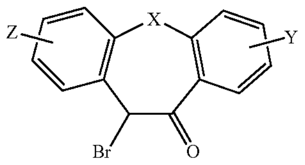

III

| X | Y | $^1$H NMR (ppm, $CDCl_3$) |
|---|---|---|
| O | H | 5.62 (s, 1H); 7.21–8.19 (m, 8H) |
| O | 8-F | 5.61 (s, 1H); 7.16–8.19 (m, 7H) |
| O | 8-Cl | 5.59 (s, 1H); 7.26–8.19 (m, 7H) |
| S | H | 6.77 (s, 1H); 7.19–8.28 (m, 8H) |
| S | 7-Cl | 6.72 (s, 1H); 7.25–8.19 (m, 7H) |
| S | 7-$CF_3$ | 6.71 (s, 1H); 7.24–8.35 (m, 7H) |
| S | 8-F | 6.79 (s, 1H); 7.05–7.97 (m, 7H) |
| S | 8-Cl | 6.71 (s, 1H); 7.11–8.27 (m, 7H) |
| S | 7-Br | 6.71 (s, 1H); 7.26–8.09 (m, 7H) |
| S | 8-Br | 6.71 (s, 1H); 7.27–8.36 (m, 7H) |
| S | 7-Cl; 8-Cl | 6.69 (s, 1H); 7.25–8.28 (m, 6H) |
| S | 8-$OCH_3$ | 3.82 (s, 3H); 6.84 (s, 1H); 7.03–7.87 (m, 7H) |

In all Examples given in the Table 5, Z=H.

What is claimed is:

1. A compound of the formula I (I)

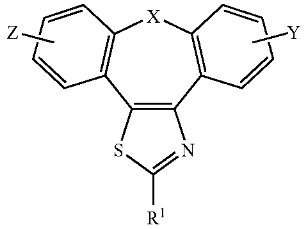

wherein

X is $CH_2$, O, S, S(=O), $S(=O)_2$, or $NR^a$, wherein $R^a$ is hydrogen or a protecting group;

Y and Z are each independently hydrogen, halogen, $C_1$-$C_4$ alkyl, $C_2$-$C_4$ alkenyl, $C_2$-$C_4$ alkynyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, N-($C_1$-$C_4$-alkyl) amino, N,N-di($C_1$-$C_4$-alkyl)amino, thiol, $C_1$-$C_4$ alkylthio, sulfonyl, $C_1$-$C_4$ alkylsulfonyl, sulfinyl, $C_1$-$C_4$ alkylsulfinyl, carboxy, $C_1$-$C_4$ alkoxycarbonyl, cyano, or nitro;

$R^1$ is hydrogen, halogen, an optionally substituted $C_1$-$C_7$ alkyl or $C_2$-$C_7$ alkenyl, $C_2$-$C_7$ alkynyl, an optionally substituted aryl, heteroaryl or heterocycle, $C_1$-$C_2$ alcohol, hydroxy, hydroxy-$C_2$-$C_7$ alkenyl, hydroxy-$C_2$-$C_7$ alkynyl, $C_1$-$C_7$ alkoxy, thiol, thio-$C_2$-$C_7$ alkenyl, thio-$C_2$-$C_7$ alkynyl, $C_1$-$C_7$ alkylthio, amino-$C_2$-$C_7$ alkenyl, amino-$C_2$-$C_7$ alkynyl, amino-$C_1$-$C_7$ alkoxy, $C_1$-$C_7$ alkanoyl, aroyl, oxo-$C_1$-$C_7$ alkyl, $C_1$-$C_7$ alkanoyloxy, carboxy, an optionally substituted $C_1$-$C_7$ alkyloxycarbonyl or $C_1$-$C_7$ aryloxycarbonyl, carbamoyl, N-($C_1$-$C_7$-alkyl)carbamoyl, N,N-di($C_1$-$C_7$-alkyl)carbamoyl, cyano, cyano-$C_1$-$C_7$ alkyl, sulfonyl, $C_1$-$C_7$ alkylsutfonyl, sulfinyl, $C_1$-$C_7$ alkylsulfinyl, nitro, or a substituent of the formula II (II)

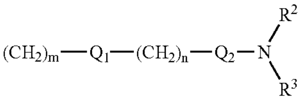

wherein $R^2$ and $R^3$ are each independently hydrogen, $C_1$-$C_4$ alkyl, or aryl or $R^2$ and $R^3$ taken together with the nitrogen atom to which they are attached form an optionally substituted heterocycle or heteroaryl;

m is an integer from 1 to 3;

n is an integer from 0 to 3;

$Q_1$ and $Q_2$ are each independently oxygen, sulfur,

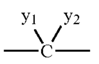 , 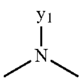 ,

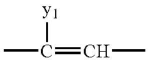 or wherein $y_1$ and $y_2$ are each independently hydrogen, halogen, an optionally substituted $C_1$-$C_4$ alkyl or aryl, hydroxy, $C_1$-$C_4$ alkoxy, $C_1$-$C_4$ alkanoyl, thiol, $C_1$-$C_4$ alkylthio, sulfonyl, $C_1$-$C_4$ alkylsulfonyl, sulfinyl, $C_1$-$C_4$ alkylsulfinyl, cyano, or nitro or $y_1$ and $y_2$ taken together with the carbon atom to which they are attached form a carbonyl or imino group;

and pharmacologically acceptable salts and solvates thereof.

2. The compound according to claim 1, wherein Y and Z are each independently H, F, Cl, Br, $CF_3$, or $OCH_3$.

3. The compound according to claim 2, wherein $R^1$ is H, $CH_3$, $CH_2CN$, CHO, $CH{=}CH_2$, $CH_2COOC_2H_5$, $COOC_2H_5$, or $CH_2OCOCH_3$.

4. The compound according to claim 1, wherein $R^1$ is an optionally substituted aryl or heteroaryl.

5. The compound according to claim 2, wherein $R^1$ is a $C_1$-$C_2$ alcohol.

6. The compound according to claim 1, wherein $R^1$ is a substituent of the formula II.

7. The compound according to claim 6, wherein m is 1 or 2, n is 1 or 2 or 3, $Q_1$ is O, $Q_2$ is $CH_2$, and $R^2$ and $R^3$ are each independently hydrogen or methyl.

8. The compound selected from the group consisting of:
8-oxa-1-thia-3-aza-dibenzo[e,h]azulene,
5-fluoro-8-oxa-1-thia-3-aza-dibenzo[e,h]azulene,
5-chloro-8-oxa-1-thia-3-aza-dibenzo[e,h]azulene;
1,8-dithia-3-aza-dibenzo[e,h]azulene;
5-chloro-2-methyl-8-oxa-1-thia-3-aza-dibenzo[e,h]azulene;
5-fluoro-2-methyl-8-oxa-1-thia-3-aza-dibenzo[e,h]azulene;
6-chloro-2-methyl-1,8-dithia-3-aza-dibenzo[e,h]azulene;
2-methyl-6-trifluoromethyl-1,8-dithia-3-aza-dibenzo[e,h] azulene;
6-bromo-2-methyl-1,8-dithia-3-aza-dibenzo[e,h]azulene;
5-bromo-2-methyl-1,8-dithia-3-aza-dibenzo[e,h]azulene;
5-chloro-2-methyl-1,8-dithia-3-aza-dibenzo[e,h]azulene;
2-methyl-1,8-dithia-3-aza-dibenzo[e,h]azulene;
2-methyl-8-oxa-1-thia-3-aza-dibenzo[e,h]azulene;
(6-chloro-1,8-dithia-3-aza-dibenzo[e,h]azulene-2-yl)-acetonitrile;
8-oxa-1-thia-3-aza-dibenzo[e,h]azulene-2-carbaldehyde;
5-fluoro-8-oxa-1-thia-3-aza-dibenzo[e,h]azulene-2-carbaldehyde;
5-chloro-8-oxa-1-thia-3-aza-dibenzo[e,h]azulene-2-carbaldehyde;
1,8-dithia-3-aza-dibenzo[e,h]azulene-2-carbaldehyde;
6-chloro-2-vinyl-1,8-dithia-3-aza-dibenzo[e,h]azulene;
(6-chloro-1,8-dithia-3-aza-dibenzo[e,h]azulene-2-yl)-acetic acid ethyl ester;
6-trifluoromethyl-1,8-dithia-3-aza-dibenzo[e,h]azulene-2-carboxylic acid ethyl ester;
5-fluoro-1,8-dithia-3-aza-dibenzo[e,h]azulene-2-carboxylic acid ethyl ester;
5-fluoro-8-oxa-1-thia-3-aza-dibenzo[e,h]azulene-2-yl-acetic acid methyl ester; and
5-chloro-8-oxa-1-thia-3-aza-dibenzo[e,h]azulene-2-yl-acetic acid methyl ester.

9. The compound selected from the group consisting of:
2-phenyl-6-trifluoromethyl-1,8-dithia-3-aza-dibenzo[e,h] azulene;
2-(4-chloro-phenyl )-6-trifluoromethyl-1,8-dithia-3-aza-dibenzo[e,h]azulene;
2-pyridine-3-yl-6-trifluoromethyl-1,8-dithia-3-aza-dibenzo[e,h]azulene;
2-pyridine-4-yl-6-trifluoromethyl-1,8-dithia-3-aza-dibenzo[e,h]azulene;
2-thiophene-3-yl-6-trifluoromethyl-1,8-dithia-3-aza-dibenzo[e,h]azulene,
2-(3-pyrrole-1-yl-phenyl)-6-trifluoromethyl-1,8-dithia-3-aza-dibenzo[e,h]azulene;
2-(3-chloro-4-fluoro-phenyl)-6-trifluoromethyl-1,8-dithia-3-aza-dibenzo[e,h]azulene;
2-(4-tert-butyl-phenyl)-6-trifluoromethyl-1,8-dithia-3-aza-dibenzo[e,h]azulene;
2-pyrazine-2-yl-6-trifluoromethyl-1,8-dithia-3-aza-dibenzo[e,h]azulene;
6-trifluoromethyl-2-(4-trifluoromethyl-phenyl)-1,8-dithia3-aza-dibenzo[e,h]azulene;
2-(4-[1,3]dioxolane-2-yl-phenyl)-6-trifluoromethyl-1,8-dithia-3-aza-dibenzo[e,h]azulene;
(6-trifluoromethyl-1,8-dithia-3-aza-dibenzo[e,h]azulene-2-yl)-(3,4,5-trimethoxy-phenyl)amine;
(3-methoxy-phenyl)-(6-trifluoromethyl-1,8-dithia-3-aza-dibenzo[e,h]azulene-2-yl)-amine;
2-(3,5-dibromo-phenyl)-6-trifluoromethyl-1,8-dithia-3-aza-dibenzo[e,h]azulene;
2-(3-fluoro-4-methyl-phenyl)-6-trifluoromethyl-1,8-dithia-3-aza-dibenzo[e,h]azulene;
2-(2,3-dihydro-benzofuran-5-yl)-6-trifluoromethyl-1,8-dithia-3-aza-dibenzo[e,h]azulene;
2-p-toluyl-6-trifluoromethyl-1,8-dithia-3-aza-dibenzo[e,h]azulene;
2-(4-[1,2,3]thiadiazole-4-yl-phenyl)-6-trifluoromethyl-1,8-dithia-3-aza-dibenzo[e,h]azulene;
2-isoxazole-5-yl-6-trifluoromethyl-1,8-dithia-3-aza-dibenzo[e,h]azulene;
2-(2-methyl-thiazole-4-yl)-6-trifluoromethyl-1,8-dithia-3-aza-dibenzo[e,h]azulene;
2-(6-methyl-pyridine-3-yl)-6-trifluoromethyl-1,8-dithia-3-aza-dibenzo[e,h]azulene, 2-(6-methoxy-pyridine-3-yl)-6-trifluoromethyl-1,8-dithia-3-aza-dibenzo[e,h] azulene;
2-(3-chloro-5-trifluoromethyl-pyridine-2-yl)-6-trifluoromethyl-1,8-dithia-3-aza-dibenzo[e,h]azulene;
2-(2,6-dichloro-benzyl)-6-trifluoromethyl-1,8-dithia-3-aza-dibenzo[e,h]azulene; 6-trifluoromethyl-2-(4-trifluoromethyl-pyridine-3-yl )-1,8-dithia-3-aza-dibenzo [e,h]azulene;
2-(2,6-dichloro-4-trifluoromethyl-phenyl)-6-trifluoromethyl-1,8-dithia-3-aza-dibenzo[e,h]azulene;
2-(2,4-dichloro-phenyl)-6-trifluoromethyl-1,8-dithia-3-aza-dibenzo[e,h]azulene;
6-trifluoromethyl-2-(3-trifluoromethyl-phenyl)-1,8-dithia-3-aza-dibenzo[e,h]azulene;
2-(5-methyl-isoxazole-3-yl)-6-trifluoromethyl-1,8-dithia3-aza-dibenzo[e,h]azulene;
2-(2-chloro-phenyl)-6-trifluoromethyl-1,8-dithia-3-aza-dibenzo[e,h]azulene;
2-(2,6-dichloro-pyridine-4-yl)-6-trifluoromethyl-1,8-dithia-3-aza-dibenzo[e,h]azulene;
6-trifluoromethyl-2-(6-trifluoromethyl-pyridine-2-yl)-1,8-dithia-3-aza-dibenzo[e,h]azulene;
2-(2,4-dichloro-phenyl)-6-trifluoromethyl-1,8-dithia-3-aza-dibenzo[e,h]azulene;
2-pyridine-4-yl-6-trifluoromethyl-8-oxa-1-thia-3-aza-dibenzo[e,h]azulene;
5,6-dichloro-2-pyridine-4-yl-1,8-dithia-3-aza-dibenzo[e,h]azulene;
2-pyridine-4-yl-8H-1-thia-3-aza-dibenzo[e,h]azulene;
5-methoxy-2-pyridine-4-yl-1,8-dithia-3-aza-dibenzo[e,h] azulene;

5-fluoro-2-pyridine-4-yl-1,8-dithia-3-aza-dibenzo[e,h]azulene;

7-chloro-2-pyridine-4-yl-1,8-dithia-3-aza-dibenzo[e,h]azulene;

7-bromo-2-pyridine-4-yl-1,8-dithia-3-aza-dibenzo[e,h]azulene;

6-chloro-2-pyridine-4-yl-1,8-dithia-3-aza-di benzo[e,h]azulene;

5-bromo-2-pyridine-4-yl-1,8-dithia-3-aza-dibenzo[e,h]azulene;

7-chloro-5-fluoro-2-pyridine4-yl-1,8-dithia-3-aza-dibenzo[e,h]azulene;

5-methyl-2-pyridine-4-yl-1,8-dithia-3-aza-dibenzo[e,h]azulene;

7-methyl-2-pyridine-4-yl-1,8-dithia-3-aza-dibenzo[e,h]azulene;

5-chloro-2-pyridine-4-yl-1,8-dithia-3-aza-dibenzo[e,h]azulene;

6-methyl-2-pyridine-4-yl-1,8-dithia-3-aza-dibenzo[e,h]azulene;

6-chloro-5-fluoro-2-pyridine-4-yl-1,8-dithia-3-aza-dibenzo[e,h]azulene; and 1-(2-pyridine-4-yl-1-thia-3,8-diaza-dibenzo[e,h]azulene-8-yl)-ethanone.

10. The compound according to claim 5 selected from the group consisting of:

(8-oxa-1-thia-3-aza-dibenzo[e,h]azulene-2-yl)-methanol;

(5-fluoro-8-oxa-1-thia-3-aza-dibenzo[e,h]azulene-2-yl)-methanol;

(5-chloro-8oxa-1-thia-3-aza-dibenzo[e,h]azulene-2-yl)-methanol;

(1,8-dithia-3-aza-dibenzo[e,h]azulene-2-yl)-methanol;

2-(6-chloro-1,8-dithia-3-aza-dibenzo[e,h]azulene-2-yl)-ethanol, (6-trifluoromethyl-1,8-dithia-3-aza-dibenzo[e,h]azulene-2-yl)-methanol; and (5-fluoro-1,8-dithia-3-aza-dibenzo[e,h]azulene-2-yl)-methanol.

11. The compound according to claim 7 selected from the group consisting of:

dimethyl-[2-(8-oxa-1-thia-3-aza-dibenzo[e, h]azulene-2-ylmethoxy)-ethyl]-amine;

dimethyl-[3-(8-oxa-1-thia-3-aza-dibenzo[e, h]azulene-2-ylmethoxy)-propyl]-amine;

3-(8-oxa-1-thia-3-aza-dibenzo[e, h]azulene-2-yl-methoxy)-propyl-amine;

[2-(5-fluoro-8-oxa-1-thia-3-aza-dibenzo[e, h]azulene-2-ylmethoxy)-ethyl]-dimethylamine;

[3-(5-fluoro-8-oxa-1-thia-3-aza-dibenzo[e, h]azulene-2-ylmethoxy)-propyl]-dimethylamine;

[2-(5-chloro-8-oxa-1-thia-3-aza-dibenzo[e, h]azulene-2-ylmethoxy)-ethyl]-dimethylamine;

[3-(5-chloro-8-oxa-1-thia-3-aza-dibenzo[e, h]azulene-2-ylmethoxy)-propyl]-dimethylamine;

[2-(1,8-dithia-3-aza-dibenzo[e, h]azulene-2-ylmethoxy)-ethyl]-dimethylamine;

[3-(1,8-dithia-3-aza-dibenzo[e, h]azulene-2-ylmethoxy)-propyl]-dimethylamine;

{3-[2-(6-chloro-1,8-dithia-3-aza-dibenzo[e,h]azulene-2-yl)-ethoxy]-propyl}-dimethylamine;

dimethyl-[2-(6-trifluoromethyl-1,8-dithia-3-aza-dibenzo[e,h]azulene-2-ylmethoxy)-ethyl]-amine;

[2-(5-fluoro-1,8-dithia-3-aza-dibenzo[e,h]azulene-2-yl-methoxy)-ethyl]-dimethylamine;

dimethyl-[3-(6-trifluoromethyl-1,8-dithia3aza-dibenzo[e,h]azulene-2-ylmethoxy)-propyl]-amine; and

[3-(5-fluoro-1,8-dithia-3-aza-dibenzo[e,h]azulene-2-yl-methoxy)-propyl]-dimethylamine.

12. A process for the preparation of a compound of the formula I (I)

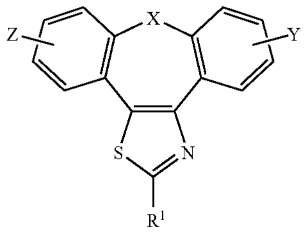

wherein

X is $CH_2$, O, S, S(═O), $S(═O)_2$, or $NR^a$, wherein $R^a$ is hydrogen or a protecting group;

Y and Z are each independently hydrogen, halogen, $C_1$-$C_4$ alkyl, $C_2$-$C_4$ alkenyl, $C_2$-$C_4$ alkynyl, halo-$C_1$-$C_4$ alkyl, hydroxy, $C_1$-$C_4$ alkoxy, trifluoromethoxy, $C_1$-$C_4$ alkanoyl, amino, amino-$C_1$-$C_4$ alkyl, N-($C_1$-$C_4$-alkyl)amino N,N-di($C_1$-$C_4$-alkyl)amino, thiol, $C_1$-$C_4$ alkylthio, sulfonyl, $C_1$-$C_4$ alkylsulfonyl, sulfinyl, $C_1$-$C_4$ alkylsulfinyl, carboxy, $C_1$-$C_4$ alkoxycarbonyl, cyano, or nitro;

$R^1$ is hydrogen, halogen, an optionally substituted $C_1$-$C_7$ alkyl or $C_2$-$C_7$ alkenyl, $C_2$-$C_7$ alkynyl, an optionally substituted aryl, heteroaryl or heterocycle, $C_1$-$C_2$ alcohol, hydroxy, hydroxy-$C_2$-$C_7$ alkenyl, hydroxy-$C_2$-$C_7$ alkynyl, $C_1$-$C_7$ alkoxy, thiol, thio-$C_2$-$C_7$ alkenyl, thio-$C_2$-$C_7$ alkynyl, $C_1$-$C_7$ alkylthio, amino-$C_2$-$C_7$ alkenyl, amino-$C_2$-$C_7$ alkynyl, amino-$C_1$-$C_7$ alkoxy, $C_1$-$C_7$ alkanoyl, aroyl, oxo-$C_1$-$C_7$ alkyl, $C_1$-$C_7$ alkanoyloxy, carboxy, an optionally substituted $C_1$-$C_7$ alkyloxycarbonyl or $C_1$-$C_7$ aryloxycarbonyl, carbamoyl, N-($C_1$-$C_7$-alkyl)carbamoyl, N,N-di($C_1$-$C_7$-alkyl)carbamoyl, cyano, cyano-$C_1$-$C_7$ alkyl, sulfonyl, $C_1$-$C_7$ alkylsulfonyl, sulfinyl, $C_1$-$C_7$ alkylsulfinyl, nitro, or a substituent of the formula II (II)

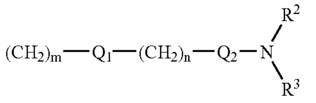

wherein $R^2$ and $R^3$ are each independently hydrogen, $C_1$-$C_4$ alkyl, or aryl or $R^2$ and $R^3$ taken together with the nitrogen atom to which they are attached form an optionally substituted heterocycle or heteroaryl;

m is an integer from 1 to 3;

n is an integer from 0 to 3;

$Q_1$ and $Q_2$ are each independently oxygen, sulfur,

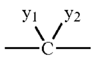 , 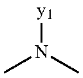 ,

-continued

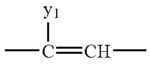

or

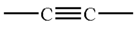

wherein $y_1$ and $y_2$ are each independently hydrogen, halogen, an optionally substituted $C_1$-$C_4$ alkyl or aryl, hydroxy, $C_1$-$C_4$ alkoxy, $C_1$-$C_4$ alkanoyl, thiol, $C_1$-$C_4$ alkylthio, sulfonyl, $C_1$-$C_4$ alkylsulfonyl, sulfinyl, $C_1$-$C_4$ alkylsulfinyl, cyano, or nitro or $y_1$ and $y_2$ taken together with the carbon atom to which they are attached form a carbonyl or imino group;

and pharmacologically acceptable salts and solvates thereof, which comprises one of the following steps (a) through (e):

a) a cyclization of an α-bromoketone of the formula III:

(III)

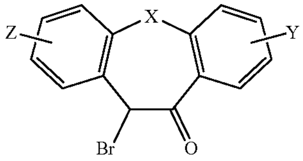

with a compound of the formula IV:

(IV)

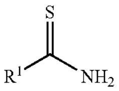

b) for a compound of the formula I, wherein $Q_1$ is —O—, a reaction of an alcohol of the formula V:

(V)

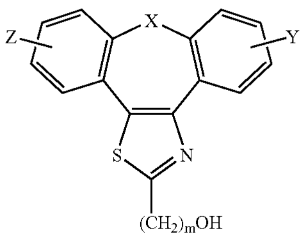

with a compound of the formula VI:

(VI)

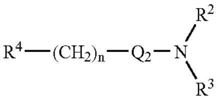

wherein $R^4$ is a leaving group;

c) for a compound of the formula I, wherein $Q_1$ is —O—, —NH—, —S— or —C≡C—, a reaction of a compound of the formula Va:

(Va)

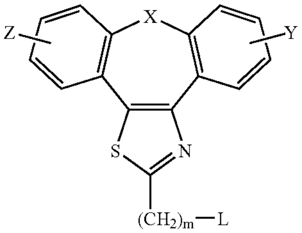

wherein L is a leaving group, with a compound of the formula VIa:

(VIa)

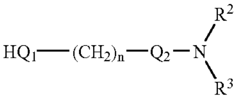

d) for a compound of the formula I, wherein $Q_1$ is —O—, —NH— or —S—, a reaction of a compound of the formula Vb:

(Vb)

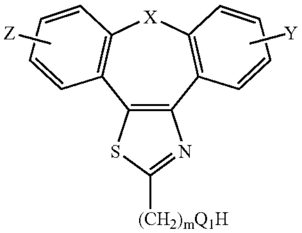

with a compound of the formula VI, wherein $R^4$ is a leaving group;

e) for a compound of the formula I, wherein $Q_1$ is —C═C—, a reaction of a compound of the formula Va, wherein $Q_1$ is carbonyl, with a phosphorous ylide.

13. A method of treating inflammation associated with TNF-α comprising administering to a subject in need thereof a an effective amount of a compound according to claim 6.

14. The method of claim 13 wherein the inflammation associated with TNF-α is inflammation associated with rheumatoid arthritis.

* * * * *